US012064469B2

(12) United States Patent
Laurie et al.

(10) Patent No.: US 12,064,469 B2
(45) Date of Patent: Aug. 20, 2024

(54) STABLE PEPTIDE COMPOSITIONS

(71) Applicants: TearSolutions, Inc., Charlottesville, VA (US); University of Virginia Patent Foundation, Charlottesville, VA (US)

(72) Inventors: Gordon W. Laurie, Charlottesville, VA (US); Marc G. Odrich, Crozet, VA (US); Michelle Carpenter, Novato, CA (US); Thomas R. Gadek, Park City, UT (US); Paul A. Laskar, Napa, CA (US)

(73) Assignees: TearSolutions, Inc., Charlottesville, VA (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 17/519,489

(22) Filed: Nov. 4, 2021

(65) Prior Publication Data

US 2022/0305083 A1    Sep. 29, 2022

Related U.S. Application Data

(63) Continuation of application No. 16/487,069, filed as application No. PCT/US2018/018775 on Feb. 20, 2018, now abandoned.

(60) Provisional application No. 62/530,565, filed on Jul. 10, 2017, provisional application No. 62/461,467, filed on Feb. 21, 2017.

(51) Int. Cl.
| A61K 38/00 | (2006.01) |
| A61K 9/00 | (2006.01) |
| A61K 38/18 | (2006.01) |
| A61K 47/02 | (2006.01) |
| A61K 47/10 | (2017.01) |
| A61K 47/12 | (2006.01) |
| A61K 47/14 | (2017.01) |
| A61K 47/18 | (2017.01) |

(52) U.S. Cl.
CPC ............ *A61K 38/18* (2013.01); *A61K 9/0014* (2013.01); *A61K 9/0048* (2013.01); *A61K 47/02* (2013.01); *A61K 47/10* (2013.01); *A61K 47/12* (2013.01); *A61K 47/14* (2013.01); *A61K 47/183* (2013.01)

(58) Field of Classification Search
None
See application file for complete search history.

(56) References Cited

U.S. PATENT DOCUMENTS

| 7,320,870 | B2 | 1/2008 | Laurie et al. |
| 7,459,440 | B2 | 12/2008 | Laurie et al. |
| 7,648,964 | B2 | 1/2010 | Laurie et al. |
| 2002/0102604 | A1 | 8/2002 | Milne Edwards et al. |
| 2002/0164669 | A1 | 11/2002 | Ruben et al. |
| 2007/0021507 | A1 | 1/2007 | Sawa et al. |
| 2007/0167371 | A1 | 7/2007 | Laurie et al. |
| 2007/0167372 | A1 | 7/2007 | Laurie et al. |
| 2007/0207522 | A1 | 9/2007 | Laurie et al. |
| 2007/0213270 | A1 | 9/2007 | Costantino et al. |
| 2008/0214456 | A1 | 9/2008 | Sosne et al. |
| 2010/0311688 | A1* | 12/2010 | Chapin .................... A61P 27/02 514/57 |
| 2011/0065189 | A1 | 3/2011 | Laurie et al. |
| 2012/0165272 | A1 | 6/2012 | Holgersson et al. |
| 2013/0005815 | A1* | 1/2013 | Sawa ...................... A61P 27/14 514/567 |
| 2016/0193301 | A1 | 7/2016 | Crockford et al. |
| 2017/0176457 | A1 | 6/2017 | Laurie |

FOREIGN PATENT DOCUMENTS

| EP | 2 270 141 A1 | 1/2011 |
| WO | WO 98/27205 A2 | 6/1998 |
| WO | WO 98/35229 A1 | 8/1998 |
| WO | WO 02/065943 A2 | 8/2002 |
| WO | WO 2004/037167 A2 | 5/2004 |
| WO | WO 2005119899 A2 | 12/2005 |
| WO | WO 2011034207 A1 | 3/2011 |
| WO | WO 2015/138604 A1 | 9/2015 |
| WO | WO-2015138604 A1 * | 9/2015 ......... A61K 38/1709 |

OTHER PUBLICATIONS

Akil et al., "Opiate binding properties of naturally occurring N- and C-Terminus modified beta-endorphins", Peptides, vol. 2, Issue 3, pp. 289-292, 1981.
Beier, et al., "Transforming growth factor beta mediates apoptosis in the ganglion cell layer during all programmed cell death periods of the developing murine retina", Neuroscience Research 56 (2006), 193-203.
Boehm et al.: "Alterations in the tear proteome of dry eye patients—A matter of the clinical phenotype.", Invest Ophthalmol Vis Sci., vol. 54, No. 3, Mar. 28, 2013 (Mar. 28, 2013), pp. 2385-2392.
Boraschi, et. al., "Interleukin-1 and Interleukin-1 Fragments as Vaccine Adjuvants", 1999, Methods, 19:108-113.
Bork, Peer; "Powers and Pitfalls in Sequence Analysis" The 70% Hurdle, Genome Research, 2000, 10: 398-400, Cold Spring Harbor Laboratory Press.
Carmona et al., "Improved Protease Stability of the Antimicrobial Peptide Pin2 Substituted with D-Amino Acids", Protein J (2013) 32:456-466.
Chen et al., "Cloning of a Novel Retinoid-inducible Serine Carboxypeptidase from Vascular Smooth Muscle Cells", The Journal of Biological Chemistry, vol. 276, No. 36, pp. 34175-34181, Sep. 2001.

(Continued)

*Primary Examiner* — Aradhana Sasan
*Assistant Examiner* — Mercy H Sabila
(74) *Attorney, Agent, or Firm* — Knobbe, Martens, Olson & Bear, LLP

(57) ABSTRACT

This application generally relates to stable peptide compositions and kits comprising low levels of buffering and chelating agents, and methods of using the same.

23 Claims, 4 Drawing Sheets

Specification includes a Sequence Listing.

(56) References Cited

OTHER PUBLICATIONS

Chesneau et al., "Isolation and Characterization of a Dibasic Selective Metalloendopeptidase from Rat Testes That Cleaves at the Amino Terminus of Arginine Residues" The Journal of Biological Chemistry, vol. 269, No. 3, Issue of Jan. 21, pp. 2056-2061, 1994.
Database EMBL Jan. 25, 1999 (Jan. 25, 1999), HSPAF93, XP002329466, accession No. AAW75083.
Database EMBL Oct. 6, 1998 (Oct. 6, 1998), XP002329465, retrieved from EMBL accession No. AAW64226.
De Souza et al., "Identification of 491 proteins in the tear fluid proteome reveals a large number of proteases and protease inhibitors", Genome Biology 2006, 7:R72.
Doerks, et. al., "Protein Annotation: Detective Work for Function Prediction", Trends in Genetics, Jun. 1998, vol. 14, No. 6: 248-250.
Engel and Lebovitz, "Peptide Hormones, Some New Developments and Their Clinical Implications", The American Journal of Medicine, vol. 35, No. 6, Dec. 1963.
Erak et al., "Peptide chemistry toolbox—Transforming natural peptides into peptide therapeutics", Bioorganic & Medicinal Chemistry 26 (2018) 2759-2765.
Fritz, Gerhard, "Molecules in focus-Human APE/Ref-1 Protein", Int. Journal of Biochemistry, 2000, 32: 925-929.
Gaudana et al., "Ocular Drug Delivery", The AAPS Journal, vol. 12, No. 3, Sep. 2010.
Hirst, et al., "High Levels of CUG-initiated FGF-2 expression cause chromatin compaction, decreased cardiomyocyte mitosis, and cell death", Molecular and Cellular Biochemistry 246: 111-116, 2003.
Im, et al., "COX-2 Regulates the insulin-like growth Factor I-induced Potentation of Zn2+-toxicity in Primary Cortical Culture", Molecular Pharmacology, 66:368-376, 2004.
Johnson et al., "Targeted Amino-Terminal Acetylation of Recombinant Proteins in E. coli", vol. 5, No. 12, Dec. 2010, e15801.
Karnati et al., "Lacritin and the tear proteome as natural replacement therapy for dry eye", Experimental Eye Research 117 (2013) 39-52.
Kumar et al., "Homo sapiens extracellular glycoprotein lacritin precursor gene, complete cds" Jan. 2, 2001, Database accession No. AY005150.
Kuranaga, et al., "Fas/Fas Ligand System in Prolactin-Induced Apoptosis in Rat Corpus Luteum: Possible Role of Luteal Immune Cells", Biochemical and Biophysical Research Communications 260, 167-173 (1999).
Laurie et al., "Lacritin Homology ECM Binding and Gene Structure", IOVS, vol. 42, No. 4, Mar. 15, 2001, pp. S260.
Laurie et al., "Detection of Prosecretory Mitogen Lacritin in Nonprimate Tears Primarily as a C-Terminal-Like Fragment", IOVS, Sep. 2012, vol. 53, No. 10, pp. 6130-6136.
Laurie et al., "Dry Eye and Designer Ophthalmics", Optometry and Vision Science, vol. 85, No. 8, pp. 643-652.
Lebovitz and Engel, "Relationships between the Structure and Biological Activities of Corticotropin and Related Peptides", Metabolism, vol. 13, No. 10—Part 2 Oct. 1964.
Ling, et al., "Progressive dopamine neuron loss following supranigral lipopolysaccharide (LPS) infusion into rats exposed to LPS prenatally", Experimental Neurology 199 (2006), 499-512.
Liu et al., Mildly acidic conditions eliminate deamidation artifact during proteolysis: digestion with endoprotease Glu-C at pH 4.5, Amino Acids, vol. 48, No. 4, pp. 1059-1067, Apr. 2016.
Lobner, et al., "Mechanisms of bFGF and NT-4 potentiation of necrotic neuronal death", Brain Research 954, (2002) 42-50.
Lumdsden, et al., "Paired Oligonucleotide Screening for BM180 in a Human Lacrimal Gland cDNA Library:Clone HL-2," American Society for Cell Biology Annual Meeting (1998).
Ma et al. Heparanase deglycanation of syndecan-1 is required for binding of the epithelial-restricted prosecretory mitogen lacritin. J Cell Biol. Sep. 25, 2006. vol. 174. No. 7. pp. 1097-1106.
Mathur et al., "PEPlife: A Repository of the Halflife of Peptides", Scientific Reports, Sci. Rep. 6, 36617; doi: 10.1038/srep36617 (2016).

Matteucci, et al., "Hepatocyte growth factor induces apoptosis through the extrinsic pathway in hepatoma cells: favouring role of hypoxia-inducible factor-1 deficiency", Oncogene (2003) 22, 4062-4073.
Mckown et al., "A Cleavage-potentiated Fragment of Tear Lacritin Is Bactericidal", The Journal of Biological Chemistry, vol. 289, No. 32, pp. 22172-22182, Aug. 8, 2014.
Mckown et al.: "Lacritin and Other New Proteins of the Lacrimal Functional Unit.", Exp Eye Res., vol. 88, No. 5., May 2009 (May 1, 2009), pp. 848-858, XP026024034, ISSN: 0014-4835.
Mishima et al., "Determination of tear volume and tear flow", IOVS, vol. 5, No. 3, pp. 264-276, Jun. 1966.
Mooradian et al., "Characterization of FN-C/H-V, a Novel Synthetic Peptide From Fibronectin That Promotes Rabbit Corneal Epithelial Cell Adhesion, Spreading, and Motility", IOVS, vol. 34, No. 1, pp. 153-164, Jan. 1993.
Morrison et al., "Modulation of retinal transducin and phosphodiesterase activities by synthetic peptides of the phosphodiesterase γ-subunit", FEBS Letters, vol. 222, No. 2, 266-270, Oct. 1987.
Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.
Pfister et al., "Synthetic Complementary Peptides Inhibit a Neutrophil Chemoattractant Found in the Alkali-injured Cornea", Cornea 19(3): 384-389, 2000.
Pham et al., "Aminopeptidase B, a glucagon-processing enzyme: site directed mutagenesis of the $Zn^{2+}$—binding motif and molecular modelling", BMC Biochemistry 2007, 8:21.
Prabhakaran, et. al., "Sequencing and Model Structure of a Naja naja atra Protein Fragment", Journal of Peptide Research, 2000, 56: 12-23.
Puig et al., "Synthetic phosphopeptide from rhodopsin sequence induces retinal arrestin binding to photoactivated unphosphorylated rhodopsin", FEBS Letters 362 (1995) 185-188.
Qi et al., "Tissue Inhibitor of Metalloproteinases-3 Peptides Inhibit Angiogenesis and Choroidal Neovascularization in Mice", PLOS ONE, vol. 8, No. 3, Mar. 2013, e55667.
Rudinger, J., et al., "Characteristics of the amino acids as components of a peptide hormone sequence", Peptide Hormones, pp. 1-7, Jun. 14, 1976.
Russo, et al., "Fibroblast Growth Factor-2 Over-Rides Insulin-like Growth Factor-I Induced Proliferation and Cell Survival in Human Neuroblastoma Cells", Journal of Cellular Physiology 199:371-380 (2004).
Sanghi et al: "Cloning, protein expression and chromosomal mapping of human lacritin (HL-2): A novel lacrimal gland secretory glycoprotein", IOVS, Mar. 15, 2000, vol. 41, No. 4, 329-B329.
Sanghi, et al., "cDNA and Genomic Cloning of Lacritin, a Novel Secretion Enhancing Factor from the Human Lacrimal Gland", Journal of Molecular Biology, Jun. 2001, vol. 310, No. 29, pp. 127-139.
Sanghi, et al., "cDNA Cloning and Expression of 'lacritin', a Novel Secreted Glycoprotein of the Lacrimal Gland", American Society for Cell Biology Annual Meeting (1999).
Sanghi, et al., "Quantitation of Rat Lacrimal Secretion: a Novel Sandwich ELISA with High Sensitivity," Experimental Eye Research, pp. 651-658 (2000).
Skolnick, et. al., "From Genes to Protein Structure and Function: Novel Applications of Computational Approaches in the Genomic Era", TIBTECH, Jan. 2000, vol. 18: 34-39.
Smith, et. al., "The Challenges of Genome Sequence Annotation or 'The Devil is in the Details'", Nature Biotechnology, Nov. 1997, vol. 15: 1222-1223.
Solovyan, et al., "Proteolytic Activation of Latent TGF-beta Precedes Caspase-3 Activation and Enhances Apoptotic Death of Lung Epithelial Cells", Journal of Cellular Physiology 207:445-453 (2006).
Sowter, et al., "Predominant Role of Hypoxia-Inducible Transcription Factor (Hif)-1 alpha versus Hif-2alpha in Regulation of the Transcriptional Response to Hypoxial", Cancer Research 63, 6130-6134, Oct. 1, 2003.

(56) References Cited

OTHER PUBLICATIONS

Stanworth et al., "Essential structural requirements for triggering of mast cells by a synthetic peptide comprising a sequence in the Cε4 domain of human IgE", Molecular Immunology, vol. 21, No. 3, pp. 243-247, Mar. 1984.
Still et al.: "Development of Quantitative Sandwich ELISAs for Lacritin and the Lacritin-c Splice Variant in Human Tears.", IOVS, Meeting Abstract, vol. 53, No. 14, Mar. 2014 (Mar. 1, 2014), XP008184852, Retrieved from the Internet <URL:http://iovs.arvojournals.org/Article.aspx?articleid=2356861> [retrieved on Jul. 9, 2015].
Stratford and Lee, "Ocular aminopeptidase activity and distribution in the albino rabbit", Current Eye Research, 4:9, 995-1000, 1985.
Van Damme et al., "Protein alpha-N-acetylation studied by N-terminomics", FEBS Journal 278 (2011) 3822-3834.
Velez et al., "Tissue Transglutaminase Is a Negative Regulator of Monomeric Lacritin Bioactivity", IOVS, Mar. 201, vol. 54, No. 3, pp. 2123-2132.
Villanueva et al., "A Sequence-specific Exopeptidase Activity Test (SSEAT) for "Functional" Biomarker Discovery", Molecular & Cellular Proteomics, vol. 7, No. 3, pp. 509-518, 2008.
Vlieghe et al., "Synthetic therapeutic peptides: science and market", Drug Discovery Today, vol. 15, Nos. 1/2, Jan. 2010.
Wang et al., "Lacrimal/salivary prosecretory mitogen 'lacritin' as a glandular stem cell survival factor", IOVS vol. 45, No. Suppl. 2, Apr. 24-29, 2004, pp. U328.
Wang et al., "Lacritin Rescues Stressed Epithelia via Rapid Forkhead Box O3 (FOXO3)-associated Autophagy That Restores Metabolism", The Journal of Biological Chemistry, vol. 288, No. 25, pp. 18146-18161, Jun. 21, 2013.
Wang et al., "Restricted epithelial proliferation by lacritin via PKCα-dependent NFAT and mTOR pathways", The Journal of Cell Biology, vol. 174, No. 5, Aug. 28, 2006, pp. 689-700.
Wells, J.A. (1990). Additivity of mutational effects in proteins. Biochemistry. 29(37):8509-8517.
Willcox et al., "A novel cationic-peptide coating for the prevention of microbial colonization on contact lenses", Journal of Applied Microbiology, vol. 105 (2008), pp. 1817-1825.
Woodley, JF, "Enzymatic barriers for GI peptide and protein delivery", Crit Rev Ther Carrier Syst. 1994; 11(2-3):61-95.
Yokoi et al., "Relationship Between Tear Volume and Tear Meniscus Curvature", Arch Ophthalmol, vol. 122, Sep. 2004, pp. 1265-1269.
Zhang et al., "Targeting of Heparanase-modified Syndecan-1 by Prosecretory Mitogen Lacritin Requires Conserved Core GAGAL plus Heparan and Chondroitin Sulfate as a Novel Hybrid Binding Site That Enhances Selectivity", The Journal of Biological Chemistry vol. 288, No. 17, pp. 12090-12101, Apr. 26, 2013.
Zhang et al: "Focus on Molecules: Syndecan-1", Experimental Eye Research, vol. 93, No. 4, Jun. 23, 2010 (Jun. 23, 2010), pp. 329-330, XP028331552, ISSN: 0014-4835, [retrieved on Jun. 23, 2010], DOI: 10.1016/J.EXER.2010.06.008.
Zhou et al., "In-depth analysis of the human tear proteome", J Prot (2012), doi: 10.1016/j.jprot.2012.04.053.
Zimmerman et al.: "The syndecans, tuners of transmembrane signaling.", FASEB J., vol. 13, 1999, pp. 91-100, XP002186787.
PCT Search Report and Written Opinion for PCT/US2015/019964, completed Jul. 8, 2015.
Chen et al., "Lacritin's active C-terminal peptide, 'Lacripep', as an efficient and innovative therapeutic for the treatment of aqueous-deficient dry eye.", Investigative Ophthalmology & Visual Science, 2015, vol. 56, ARVO Annual Meeting Abstract, #300, https://iovs.arvojournals.org/article.aspx? articleid=2332827.

* cited by examiner

STABLE PEPTIDE COMPOSITIONS

CROSS-REFERENCE TO RELATED APPLICATIONS

This application is a continuation of U.S. patent application Ser. No. 16/487,069, filed on Aug. 19, 2019, which is a U.S. National Phase Application of PCT International Application Number PCT/US2018/018775, filed on Feb. 20, 2018, designating the United States of America and published in the English language, which claims priority to U.S. Provisional Patent Application No. 62/530,565, filed Jul. 10, 2017, and to U.S. Provisional Patent Application No. 62/461,467, filed Feb. 21, 2017, each of which is herein incorporated by reference in its entirety.

STATEMENT REGARDING FEDERALLY SPONSORED R&D

This invention was made with government support under R01EY024327 awarded by the National Institute of Health. The government has certain rights in the invention.

REFERENCE TO SEQUENCE LISTING

The material in the accompanying sequence listing is hereby incorporated by reference into this application. The accompanying sequence listing text file, named TEAR.003WO.TXT, was created on Feb. 14, 2018 and is 7.18 KB. The content of the sequence listing is hereby incorporated by reference in its entirety.

BACKGROUND

Field

The present application relates to the fields of chemistry, biochemistry and medicine. More particularly, several embodiments of the present application relate to stable, dilute peptide compositions and kits comprising such compositions. Specifically, several embodiments of the present application describe compositions comprising an aqueous solution of citrate, EDTA, and a peptide, which are stable at room temperature (e.g., 20° C. to 25° C.), with or without a surfactant.

Description of the Related Art

Polypeptides are increasingly being recognized as potential therapeutic agents. Consequently, there is an increased interest in exploring polypeptides in pharmaceutical research and development. However, polypeptides are notoriously difficult to formulate and additives used to preserve or stabilize such formulations result in, for example, undesired side effects.

SUMMARY

There is an unmet need for peptide compositions that provide therapeutic amounts of peptides, are stable at room temperature, and contain only trace amounts of stabilizers and/or preservatives, or none at all. To address such needs and others, several embodiments of the present application provide stable polypeptide compositions. Advantageously, in some embodiments, the peptide (or combination of peptides) is stabilized in the compositions of the present application so as to allow for long-term storage and/or delivery over a prolonged period of time. As such, these peptide compositions are stable at non-refrigerated temperatures without the need for reconstitution, and are functional over a range of temperatures, including temperatures ranging from 0-30° C. Indeed, certain embodiments of this application are based, in part, on the surprising and unexpected discovery that dilute peptide compositions including low levels of EDTA in combination with low levels of citrate buffer remain efficacious after storage at room temperature, even though such compositions contain additive levels substantially lower than typically found in polypeptide compositions.

Some embodiments provide a composition (e.g., liquid) composition comprising, consisting or consisting essentially of about 0.00001%-0.1%, 0.001%-0.1% (e.g., 0.01% or 0.005% or 0.001%) of a polypeptide, or a pharmaceutically acceptable salt thereof; about 0.03%-3% (e.g., 0.2888%) of a buffer; no, or about 0.0001%-0.01% (e.g., 0%, or 0.001%) disodium EDTA; no, or about 0.005%-0.5% (e.g., 0%, or 0.05%) tyloxapol, and sodium chloride (e.g., 0.5%); wherein the pH of the composition is between about 6.2 to about 6.8 and the osmolality of the composition is between about 150-500 mOsm/kg or higher (e.g., 250 to 350) mOsm/kg. Liquid compositions include, but are not limited to, combinations, mixtures, solutions, gel compositions and ointments.

In some embodiments, the buffer is a citrate buffer. In some embodiments, the citrate buffer comprises about 0.001%-0.1% (e.g., 0.0098%) anhydrous citric acid and about 0.02%-2% (e.g., 0.279%) sodium citrate dihydrate. In some embodiments, the pH of the composition is about 6.5.

In some embodiments, the osmolality of the composition is between about 280 to about 320 mOsm/kg. In some embodiments, the osmolality of the composition is about 300 mOsm/kg. In some embodiments, the amount of NaCl is between 0.4% and 0.6% (e.g., about 0.5%).

In some embodiments, the composition further comprises paraben such as methylparaben (e.g., 0.04% or less). In alternate embodiments, no parabens or other preservatives are included. In some embodiments, the composition further comprises sodium chlorite.

Some embodiments provide a kit, comprising a plurality of sterile single-use 3 containers, wherein each container comprises a vessel for holding the composition. In some embodiments, the container comprises between about 0.03 mL to about 1 mL (e.g., 0.040 mL, 0.050 mL, 0.060 mL, 0.070 mL, 0.075 mL, 0.1 mL, 0.15 mL, 0.2 mL, 0.25 mL 0.3 mL, 0.35 mL, 0.4 mL, 0.45 mL, 0.5 mL, 0.6 mL, 0.7 mL, 0.8 mL, 0.9 mL) of the composition. In some embodiments, the container is for daily use, weekly use or more long-term use. In one embodiment, a 1 mL-30 mL container is used. The containers, in some embodiments are drop bottles or gel/ointment tubes. In some embodiments, the container comprises a removable seal top for sealing the vessel, and a neck portion interconnecting the vessel and the seal top.

In some embodiments, the container is made from one or more of the following materials: polyvinyl chloride, polypropylene, polyethylene terephthalate, polyethylene terephthalate, polyethylene terephthalate G, high-density polyethylene, low-density polyethylene, polybutylene terephthalate, polyurethane, polyethylene vinyl acetate, silicone, acrylonitrile butadiene styrene, polytetrafluoroethylene, polycarbonate, polystyrene, polymethylmethacrylate, polysulfone, polyvinylidene chloride, or combinations thereof. Glass containers and surfaces that reduce the adhesion of the composition to the inner container surface are provided in some embodiments.

In some embodiments, the polypeptide is Lacripep™ having SEQ ID NO: 1, or a pharmaceutically acceptable salt thereof. In some embodiments, the polypeptide has a sequence selected from the group of SEQ ID NOs: 2-9, or pharmaceutically acceptable salt, or a fragment or fragments, thereof. In some embodiments, the polypeptide, or a pharmaceutically acceptable salt thereof, has sequence homology of at least about 80%, 85% 90%, 95%, or 98% to SEQ ID NO: 1 or SEQ ID NOs: 2-9.

Some embodiments provide a method of administration comprising topically applying the composition to the eye, such as a liquid eye drop from a single-use container. Some embodiments provide a method of administration comprising topically applying the composition to the eye, such as a sterile unpreserved liquid eye drop from a single-use container.

Some embodiments provide a method of treating Dry Eye and/or Primary Sjogren's Syndrome comprising administering the compositions disclosed herein to the eye of a subject having Dry Eye and/or Primary Sjogren's Syndrome, where the polypeptide or pharmaceutically acceptable salt thereof is in an amount of 0.005%, or 0.01%, where the polypeptide has a sequence consisting of Ac-Lys-Gln-Phe-Ile-Glu-Asn-Gly-Ser-Glu-Phe-Ala-Gln-Lys-Leu-Leu-Lys-Lys-Phe-Ser-$NH_2$, where "Ac" represents an acetyl group and the C-terminus is amidated (SEQ ID NO: 1), and where one drop is administered to the eye of the subject up to three times daily. In some embodiments the administration improves the Fluorescein corneal staining (FCS) total score (NEI/Industry Workshop 0-15 scale) in the subject's eye after at least two weeks of treatment, or after at least four weeks of treatment, or after at least six weeks from the start of four weeks of treatment, compared to a baseline measure prior to starting treatment. In some embodiments, the administration improves one or more of:

eye dryness after at least two weeks of treatment, or after at least four weeks of treatment, compared to baseline on a visual analog scale;
SANDE (global scores SANDE 1) after at least two weeks of treatment compared to a baseline measure prior to starting treatment;
Mean Scores for SANDE (global scores SANDE-1) after at least two weeks of treatment compared to a baseline measure prior to starting treatment;
Individual Symptom Assessments (Instantaneous) after at least two weeks of treatment compared to a baseline measure prior to starting treatment;
Mean Scores for Individual Symptom Assessments (Reflective) after at least two weeks of treatment compared to a baseline measure prior to starting treatment;
LGCS in the subject's eye after at least two weeks of treatment compared to a baseline measure prior to starting treatment;
Anesthetized Schirmer test in the subject's eye after at least two weeks of treatment compared to a baseline measure prior to starting treatment;
TFBUT in the subject's eye after at least two weeks of treatment compared to a baseline measure prior to starting treatment;
FCS in the subject's eye after at least two weeks of treatment compared to a baseline measure prior to starting treatment;
SANDE (global scores for SANDE 1) after at least 2 weeks of treatment, or after at least 4 weeks of treatment, or 1 week after 4 weeks treatment compared to a baseline measure prior to starting treatment;
Individual Symptoms (Instantaneous) after at least 2 weeks of treatment, or after at least 4 weeks of treatment, or 1 week after 4 weeks treatment compared to a baseline measure prior to starting treatment;
Mean Scores for (global scores SANDE-2) after at least 2 weeks of treatment, or after at least 4 weeks of treatment, or 1 week after 4 weeks treatment compared to a baseline measure prior to starting treatment;
Mean Scores for Individual Symptom Assessments (Reflective) after at least 2 weeks of treatment, or after at least 4 weeks of treatment, or 1 week after 4 weeks treatment compared to a baseline measure prior to starting treatment;
FCS and SANDE 1 and Individual Symptom Assessments (Instantaneous) after at least 2 weeks of treatment, or after at least 4 weeks of treatment, compared to a baseline measure prior to starting treatment;
LGCS after at least 2 weeks of treatment, or after at least 4 weeks of treatment compared to a baseline measure prior to starting treatment;
Anesthetized Schirmer test results after at least 2 weeks of treatment, or after at least 4 weeks of treatment, compared to a baseline measure prior to starting treatment;
TFBUT after at least 2 weeks of treatment, or after at least 4 weeks of treatment, or 1 week after 4 weeks treatment compared to a baseline measure prior to starting treatment.

In some embodiments the administration of the composition to a group of subjects does not result in a rate of adverse events that is statistically higher compared to a rate of adverse events for administration of placebo to a similar group of subjects. In some embodiments administration of the composition to a group of subjects does not result in a rate of severe adverse events that is statistically higher compared to a rate of severe adverse events for administration of placebo to a similar group of subjects. In some embodiments the concentration of polypeptide or pharmaceutically acceptable salt thereof is about 0.005%. In some embodiments the concentration of polypeptide or pharmaceutically acceptable salt thereof is about 0.01%. In some embodiments the subject meets all the following criteria:

age 18 years of age or older;
a documented prior history or current diagnosis of Primary Sjogren's Syndrome per the American-European Consensus Group Sjogren's Syndrome Criteria, having either 4 out of 6 total criteria or 3 out of 4 signs;
if the subject is on systemic (oral) therapy for the treatment of Sjogren's Syndrome, the subject must be on stable systemic treatment defined as the same treatment for the immediately prior 90 days;
a history of dry eye-related ocular symptoms, and who has self-reported use of over the counter ocular wetting agents within the last 120 days; and
meet all the following criteria at prior to beginning treatment:
a) Fluorescein corneal staining (FCS) total score≥4 and <15 in the National Eye Institute (NEI)/Industry Workshop scale (where 0=no staining);
b) Symptom score of ≥40 using the SANDE questionnaire;
c) Anesthetized Schirmer test score≤5 mm wetting/5 min;
d) Lissamine green conjunctival staining (LGCS) total score≥5 using the NEI/Industry Workshop scale, (where 0=no staining);

wherein the Subject must meet all 4 criteria in at least one and the same eye at the time of the visit.

In some embodiments the subject does not meet one or more of the following criteria:

any active infectious ocular condition;
monocular or have a Best Corrected Visual Acuity (BCVA), using corrective lenses if necessary, of +1.0 log MAR or worse as assessed by Early Treatment Diabetic Retinopathy Study (ETDRS);
ocular inflammatory conditions (e.g., conjunctivitis, keratitis, anterior blepharitis, etc.) not related to dry eye syndrome;
clinical evidence of cicatricial ocular surface disease, such as cicatricial ocular pemphigoid or Stevens Johnson syndrome;
cannot suspend the use of any topical eye medications (including topical cyclosporine, and/or topical corticosteroids) during treatment with the composition;
has used Restasis® (topical ophthalmic cyclosporine) within 60 days prior to beginning treatment with the composition;
has used Xiidra® (topical ophthalmic lifitegrast) within 30 to 60, or 60 days prior to beginning treatment with the composition;
the subject's eye has fluorescein corneal staining (FCS) total score=15 or a score=3 in the superior region NEI/Industry Workshop scale or the subject's eye has FCS with diffuse confluent staining, filaments or frank epithelial defects;
has active or have had an outbreak of herpetic keratitis within 365 days of Beginning treatment or subjects who are on chronic oral antivirals for herpetic disease;
cannot suspend the use of and abstain from contact lens use during treatment;
has a history of collagen vascular disease, auto immune disease or rheumatic disease other than Primary Sjogren's Syndrome (e.g., Lupus, Rheumatoid Arthritis, etc.);
has a history of or current Anterior Membrane Dystrophy;
has had a corneal transplant or similar corneal surgery (DALK, DSEK, DMEK, etc.);
has used or anticipate use of amiodarone;
within 30 days prior to beginning treatment alter the dose or anticipate alterations to the dose of the following: tetracyclines, Omega 3 or Omega 6;
who within 60 days prior to beginning treatment and/or for the duration of treatment, altered the dose or anticipate alterations to the dose of the following: anticholinergics, antidepressants, oral contraceptives, isotretinoin, oral systemic corticosteroids, oral systemic immunosuppressive agents,
within 30 days prior to beginning treatment and/or for the duration of the study have used topical ocular antihistamines, ocular, inhaled or intranasal corticosteroids, topical or oral mast cell stabilizers, oral antihistamines, topical or nasal vasoconstrictors, topical ocular NSAIDs, topical ocular antibiotics;
in the subject's eye and within the past 90 days have had cauterization of the punctum or alterations to (insertion or removal) punctal plug(s) before beginning treatment;
in the subject's eye, have had corneal refractive surgery (LASIK, PRK, RK);
a history of any operative procedure on the ocular surface or eyelids within 365 days prior to beginning treatment with a history of intraocular surgery within 90 days prior to beginning treatment;
is pregnant or suspected to be pregnant;
is breastfeeding or intend to breastfeed; and
has participated in a device or investigational drug study or clinical trial within 30 days of beginning treatment.

In some embodiments of any of the compositions, kits or methods disclosed herein, the polypeptide has a sequence consisting of Ac-Lys-Gln-Phe-Ile-Glu-Asn-Gly-Ser-Glu-Phe-Ala-Gln-Lys-Leu-Leu-Lys-Lys-Phe-Ser-NH$_2$, where "Ac" represents an acetyl group and the C-terminus is amidated (SEQ ID NO: 1). In some embodiments of any of the compositions, kits or methods disclosed herein, the amount of polypeptide of pharmaceutically acceptable salt thereof is 0.01% or 0.005%. In some embodiments, the comparison to a baseline measure prior to starting treatment instead or further comprises a comparison of treatment with said polypeptide relative a vehicle control. In some embodiments of any of the compositions, kits or methods disclosed herein, the composition contains no tyloxapol. In some embodiments of any of the compositions, kits or methods disclosed herein, the composition contains no EDTA. In some embodiments of any of the compositions, kits or methods disclosed herein, the composition maintains at least about 99.0% of the polypeptide in undegraded form in said composition after storage of said composition for 1 week at 5±3° C. or 25±2° C. and 25±5% relative humidity. In some embodiments of any of the compositions, kits or methods disclosed herein, the composition maintains at least about 99.0% of the polypeptide in undegraded form in said composition after storage of said composition for 2 weeks at 25±2° C. and 25±5% relative humidity. In some embodiments of any of the compositions, kits or methods disclosed herein, the composition maintains at least about 99.0% of the polypeptide in undegraded form in said composition after storage of said composition for 1 month at 5±3° C. or 25±2° C. and 25±5% relative humidity. In some embodiments of any of the compositions, kits or methods disclosed herein, the composition maintains at least about 99.0% of the polypeptide in undegraded form in said composition after storage of said composition for 2 months at 5±3° C. In some embodiments of any of the compositions, kits or methods disclosed herein, the composition maintains at least about 99.0% of the polypeptide in undegraded form in said composition after storage of said composition for 3 months at 5±3° C. or −20±5° C. In some embodiments of any of the compositions, kits or methods disclosed herein, composition maintains at least about 99.0% of the polypeptide in undegraded form in said composition after storage of said composition for 4 months at 5±3° C. In some embodiments of any of the compositions, kits or methods disclosed herein, the composition maintains at least about 99.0% of the polypeptide in undegraded form in said composition after storage of said composition for 5 months at 5±3° C. In some embodiments of any of the compositions, kits or methods disclosed herein, the composition maintains at least about 99.5%, 99.9%, or 99.95% of the polypeptide in undegraded form in said composition. In some embodiments of any of the compositions, kits or methods disclosed herein, the composition maintains at least about 80% or 90% of the polypeptide in undegraded form in said composition after storage of said composition for 12 months at 5±3° C.

Figure 1A:
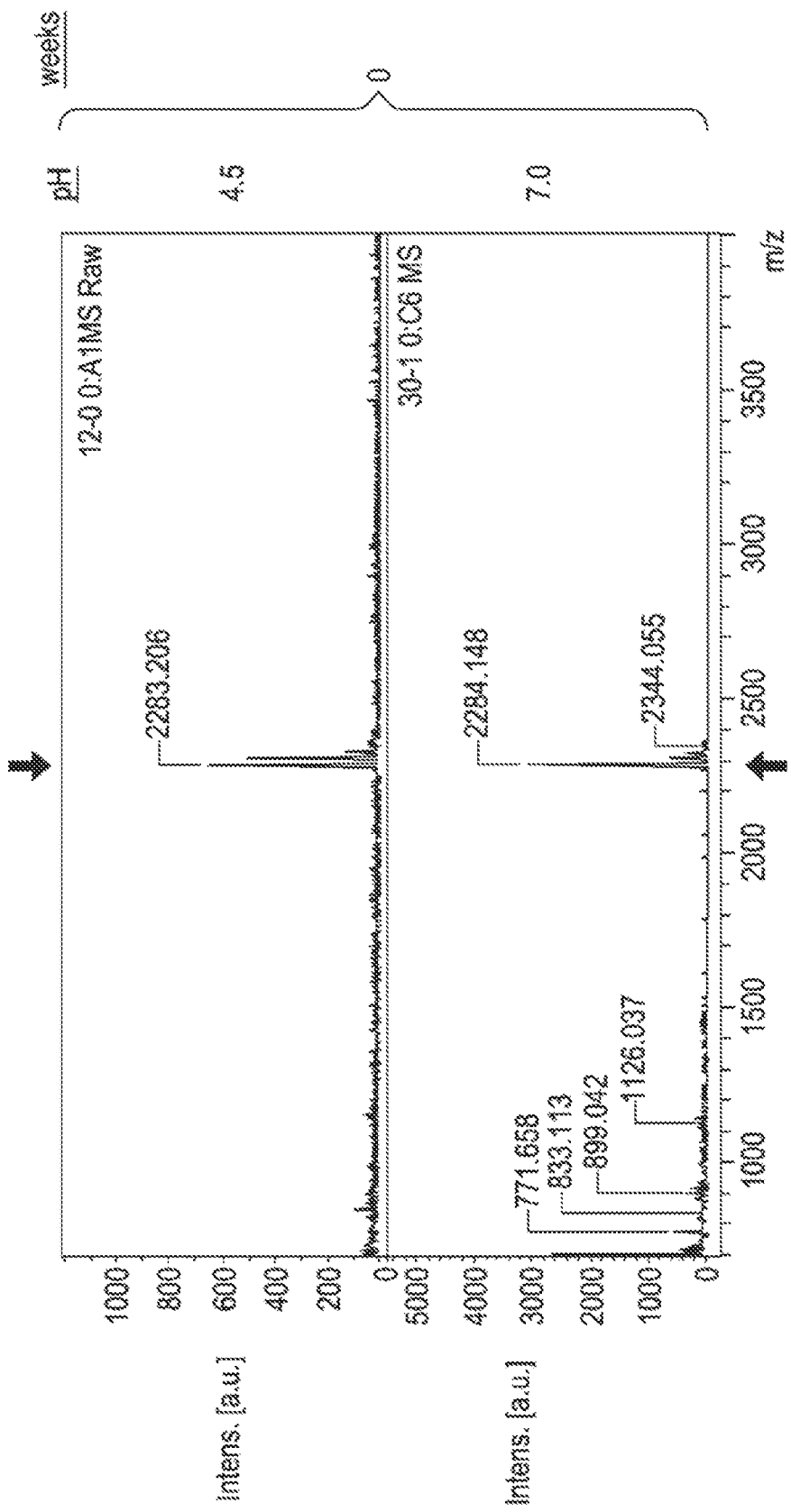
FIGS. 1A and 1B illustrate the stability of Lacripep™ (SEQ ID NO: 1) (0.001%) in phosphate buffered saline (PBS), pH 4.5 and 7.0. The Lacripep™ solutions were analyzed by MALDI TOF mass spectrometry at time 0 (FIG.
Figure 1B:
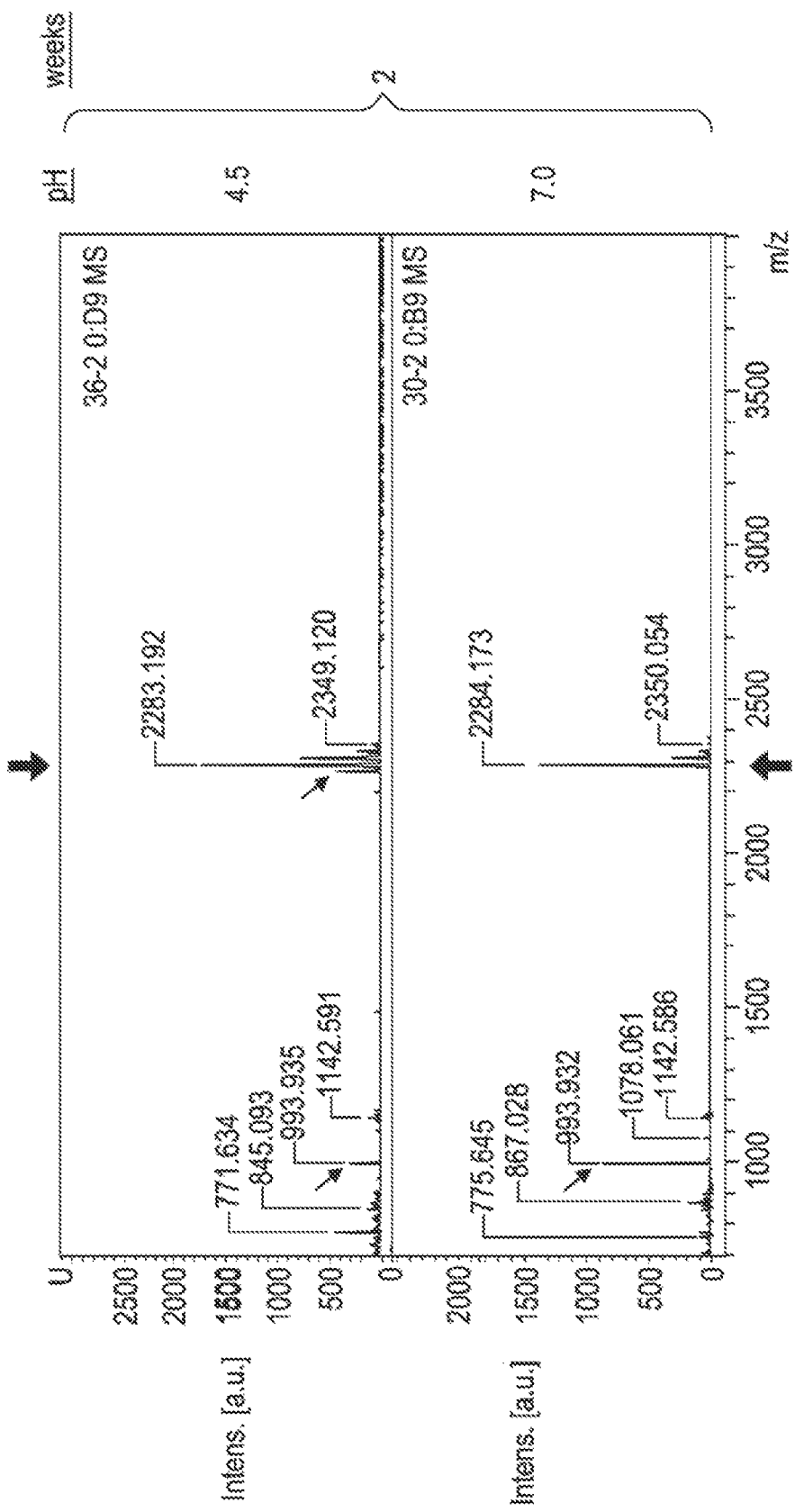

1A) and after two weeks (FIG. 1B) at 60° C. After 2 weeks, a peak at 993.9 (m/e) (indicated by arrow) corresponding to a degradation product becomes apparent at the expense of the Lacripep™ peak in both the pH 4.5 and 7.0 solutions. An additional degradation product is seen in the pH 4.5 solution at about 2270 (m/e) (indicated by arrow).

Figure 2A:
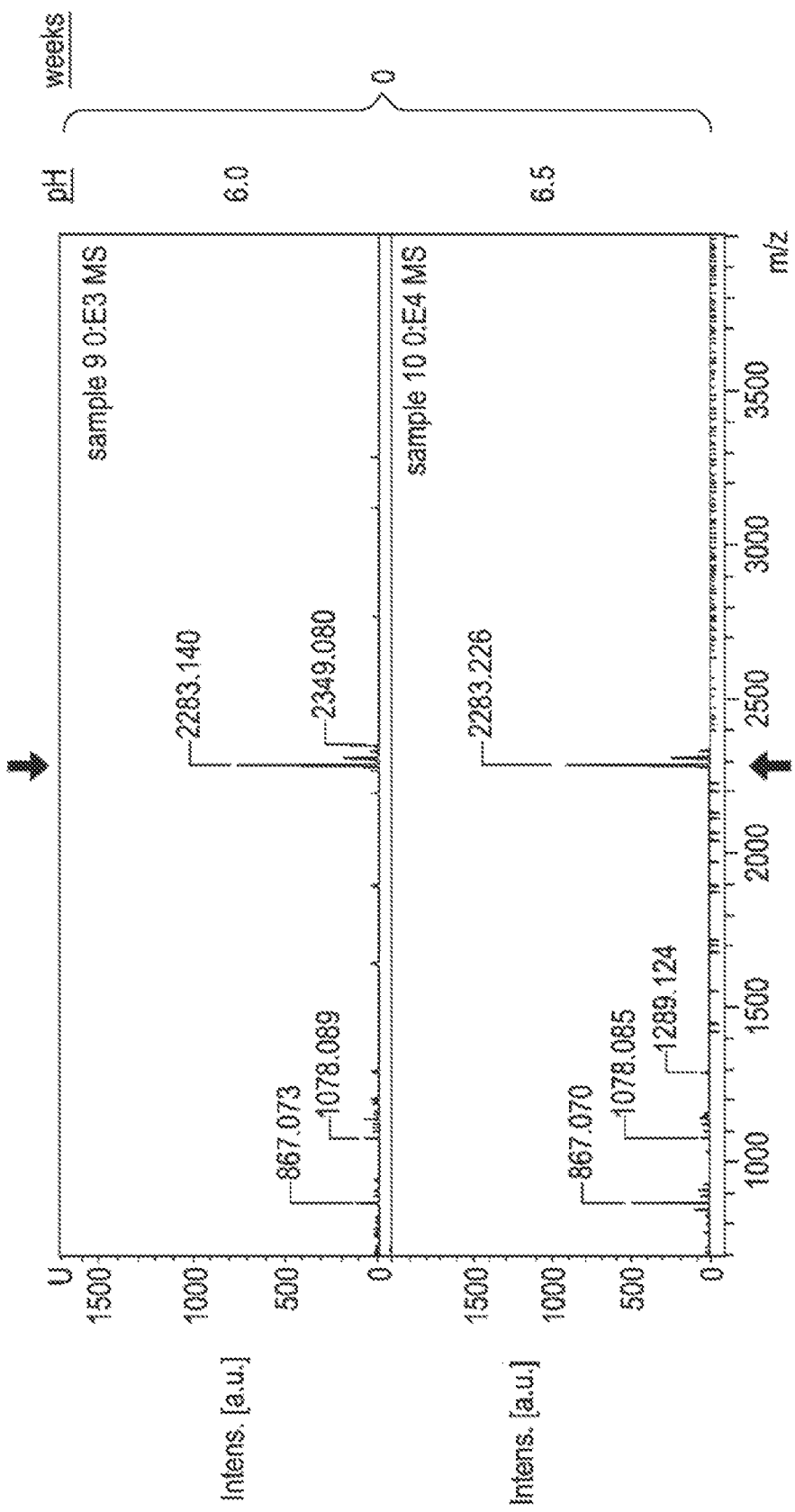
Figure 2B:
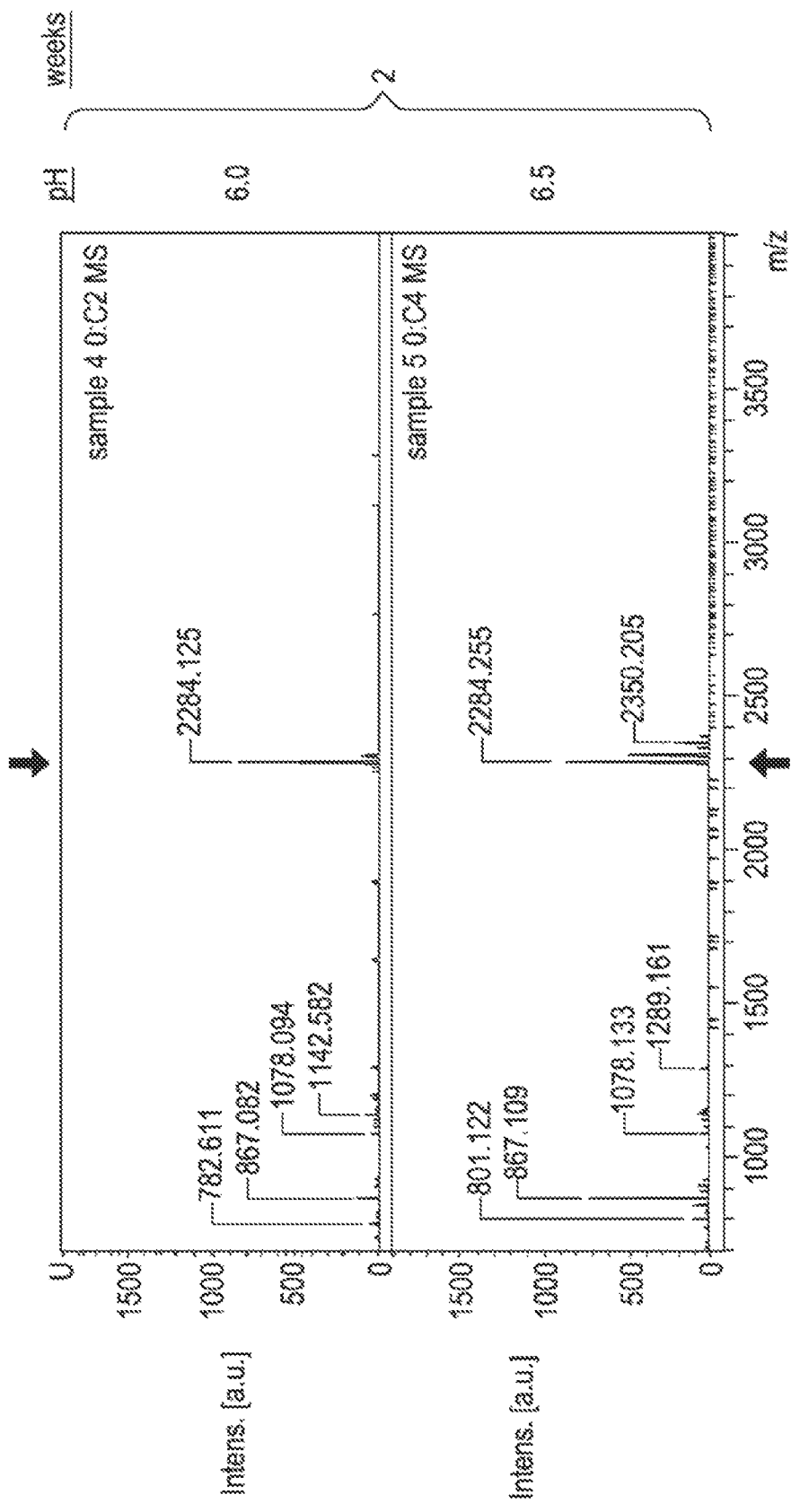

FIGS. 2A and 2B illustrate the superior stability of Lacripep™ (SEQ ID NO: 1) (0.001%) in citrate buffer at pH 6 and 6.5. The Lacripep™ solutions were analyzed by MALDI TOF mass spectrometry at time 0 (FIG. 2A) and after two weeks (FIG. 2B) at 60° C. After 2 weeks, there is no change in the intensity of the Lacripep™ peak (indicated by an arrow), and no significant increase in lower mass to charge ratio peaks.

DETAILED DESCRIPTION

Definitions

The following are illustrative definitions of terms used herein. Unless expressly stated otherwise, all technical and scientific terms used herein have the same meaning as is commonly understood by one of ordinary skill in the art read in light of the entire specification. All patents, applications, published applications and other publications referenced herein are incorporated by reference in their entirety unless stated otherwise.

The term "about," as used herein, refers to a quantity, value, number, frequency, percentage, amount, or weight that varies±10% to a reference quantity, value, number, frequency, percentage, amount, or weight.

Unless indicated otherwise, when a percentage (%) value is used in the present application, the value refers to a weight/weight percent value.

The term "tonicity agent" as used herein, shall be given its ordinary meaning and shall include materials whose primary purpose is to alter the osmolality of a composition. Suitable tonicity agents include, but are not limited to, propylene glycol, polyethylene glycols, sodium chloride, potassium chloride, magnesium chloride, calcium chloride, simple sugars such as dextrose, fructose, galactose, and/or simple polyols such as the sugar alcohols mannitol, sorbitol, xylitol, lactitol, isomaltitol, maltitol, hydrogenated starch hydrolysates, glycerin, and combinations of the foregoing.

The term "stabilizing agent" as used herein shall be given its ordinary meaning and shall include a material that inhibits chemical reactions with a peptide. Stabilizing agents may include, for example, antioxidants such as sodium metabisulfite, sodium thiosulfate, acetylcysteine, butylated hydroxyanisole, butylated hydroxytoluene, and combinations of the foregoing.

The term "surfactant" as used herein shall be given its ordinary meaning and shall include amphiphilic molecules, meaning that they contain both hydrophobic groups (tails) and hydrophilic groups (heads). Therefore, a surfactant contains both a water insoluble (or oil soluble) component and a water soluble component. As used herein, surfactants may be detergents, wetting agents, emulsifiers, foaming agents, or dispersants. In some embodiments, the polypeptide can act as a surfactant.

The term "chelating agent," as used herein shall be given its ordinary meaning and shall include a compound that can form two or more bonds to a metal ion, i.e., a multi-dentate ligand. Chelating agents include, but are not limited to ethylenediaminetetraacetic acid (EDTA), ethylenediamine, amino acids such as glutamic acid and histidine, organic diacids such as oxalic acid, malonic acid, succinic acid, and the like, and pharmaceutically acceptable salts of the foregoing. In several embodiments, a chelating agent is EDTA, or a pharmaceutically acceptable salt thereof. In some embodiments, the polypeptide can act as a chelator.

The term "viscosity building agent" as used herein, shall be given its ordinary meaning and shall include materials that affect the viscosity (centipoise, or Cp) of a composition. Examples of viscosity enhancing agents include, but are not limited to: polysaccharides, such as hyaluronic acid and its salts, chondroitin sulfate and its salts, dextrans, various polymers of the cellulose family (and derivatives thereof), vinyl polymers, and acrylic acid polymers. Non-limiting examples of viscosity building agents include polyvinylalcohol (PVA), polyvinylpyrrolidone (PVP), polyethylene glycol (PEG), and polyacrylic acid (PAA).

The term "ophthalmically acceptable" as used herein shall be given its ordinary meaning and shall include materials that are compatible with ocular tissue; that is, it does not cause significant or undue detrimental effects when brought into contact with ocular tissue.

The terms "stable," "stability" or "stabilized" as used herein shall be given their ordinary meaning and shall include products and compositions that enhance the primary, secondary and/or tertiary structure of the polypeptide. In some embodiments, stabilized compositions may have an acceptable percentage of peptide degradation, or aggregation, products after a given period of time. These peptide degradation products can be the result of, for example, oxidation and/or hydrolysis of the peptide.

The terms "peptide", "polypeptide" and "protein" as used herein, are used interchangeably and shall be given its ordinary meaning. Unless otherwise clear from the context, the noted terms include a polymer having at least two amino acids linked through peptide bonds. The terms thus include oligopeptides, analogs, derivatives, acetylated derivatives, glycosylated derivatives, pegylated derivatives, and the like.

The term "pharmaceutically acceptable salt" shall be given its ordinary meaning and shall include a salt of a compound that does not cause significant irritation to an organism to which it is administered and does not abrogate or substantially reduce the biological activity and properties of the compound. In some embodiments, the salt of the compound may enhance the biological activity and properties of the compound. In other embodiments, the salt may additionally enhance the structural integrity or chemical stability of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, or phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine. In some embodiments, the polypeptide is an acetate salt.

ADVANTAGES IN SEVERAL EMBODIMENTS

As described above and herein, several embodiments of the application provide compositions that are stable at room temperature. In several embodiments, the compositions have reduced levels of stabilizers and other additives that may cause undesired side effects, and yet still provide the desired stability. In some embodiments, the composition provides stability in the eye, nasal cavity, mouth, epithelium and other tissues for up to 1, 3, 6, 12, 24 and 48 hours. In some embodiments, the composition is formulated such that some or all of the ingredients do not evaporate, become absorbed, drained or otherwise eliminated after application to the eye or other region, and instead remain stable and active for several hours (e.g., 1-3 hours, 3-6 hours, 6-12 hours, 12-24 hours, and ranges therein). In some embodiments, the composition comprises a peptide, for example Lacripep™ or the other sequences identified herein, where the peptide is applied to the eye, and the peptide is integrated into the lipid layer of the tear covering the eye, or at the interface of the lipid and aqueous components of the tear, where the peptide stabilizes the tear and remains in the tear for a period of at least 1-3 hours, at least 3-6 hours, or at least 12-24 hours, or more than 24 hours. This feature, in several embodiments, is particularly advantageous because it allows an active ingredient (such as a peptide) to remain stable and efficacious for prolonged periods of time. In some embodiments, reduced frequency of administration results in an overall reduced overall burden of ingredients to sensitive areas of the body (such as the eye).

Although peptides are provided in several embodiments herein, other compounds may be used as the active ingredient in addition to or in lieu of a peptide.

Peptides are highly selective and efficacious and, at the same time, relatively safe and well tolerated. Peptides are particularly well-suited for the compositions described herein because peptides may be chemically and physically unstable, relative to certain small-molecule-based therapeutics. For example, peptides are prone to hydrolysis, oxidation, and aggregation. Polypeptide compositions are typically aqueous solutions containing the active peptide along with numerous stabilizers, preservatives, and other agents to maintain the efficacy of the peptide. The stabilizers, preservatives, and other agents may maintain the chemical and/or structural integrity of the polypeptide, thus preserving its efficacy. Certain additives, such as stabilizers and preservatives, may cause undesirable side-effects, including hypersensitivity reactions, itching, and stinging or burning. However, to maximize the shelf-life of the peptide and maintain efficacy, these additives are required in most peptide compositions in amounts that cause undesired results. Even in compositions with all these additives, peptide therapeutics must typically be refrigerated, making transportation difficult, and, even with refrigeration, still have a short shelf-life. Moreover, as the peptides degrade and/or aggregate over time (especially through warming and cooling when taken from cold storage to room temperature for use), the by-products may not only be inactive, they may be toxic and/or immunogenic. Formulators may attempt to increase potency of peptide compositions by increasing the amount of the active peptide in the composition. However, increased peptide concentration also increases the rate of peptide aggregation and inactivation.

Thus, several embodiments herein provide peptide compositions that provide therapeutic amounts of peptides, are stable at room temperature, and contain reduced (e.g., only trace amounts) of stabilizers and/or preservatives, or none at all.

In some embodiments, the peptide is selected from the group consisting of: (a) The amino acid sequence KQFIENGSEFAQKLLKKFS, Ac-KQFIENGSE-FAQKLLKKFS-NH$_2$, or Ac-Lys-Gln-Phe-Ile-Glu-Asn-Gly-Ser-Glu-Phe-Ala-Gln-Lys-Leu-Leu-Lys-Lys-Phe-Ser-NH$_2$, where "Ac" represents an acetyl group and the C-terminus is amidated (SEQ ID NO: 1), also referred to herein as "Lacripep™"; and, (b) the amino acid sequence KQFIENG-SEFAQKLLKKFSLLKPWA, Ac-KQFIENGSE-FAQKLLKKFSLLKPWA-NH$_2$, or Ac-Lys-Gln-Phe-Ile-Glu-Asn-Gly-Ser-Glu-Phe-Ala-Gln-Lys-Leu-Leu-Lys-Lys-Phe-Ser-Leu-Leu-Lys-Pro-Trp-Ala-NH$_2$, where "Ac" represents an acetyl group and the C-terminus is amidated (SEQ ID NO: 2). In other embodiments, the peptide has the amino acid sequence of one of the following, or a fragment thereof, optionally with the N-terminus acetylated and/or the C-terminus amidated:

```
<210> SEQ ID NO 3
<211> LENGTH: 138
<212> TYPE: PRT
<213> ORGANISM: Homo sapiens
<400> SEQUENCE: 3
      Met Lys Phe Thr Thr Leu Leu Phe Leu Ala Ala Val Ala Gly Ala Leu
      1               5                   10                  15

Val Tyr Ala Glu Asp Ala Ser Ser Asp Ser Thr Gly Ala Asp Pro Ala
                      20                  25                  30

Gln Glu Ala Gly Thr Ser Lys Pro Asn Glu Glu Ile Ser Gly Pro Ala
                  35                  40                  45

Glu Pro Ala Ser Pro Pro Glu Thr Thr Thr Thr Ala Gln Glu Thr Ser
              50                  55                  60

Ala Ala Ala Val Gln Gly Thr Ala Lys Val Thr Ser Ser Arg Gln Glu
      65                  70                  75                  80

Leu Asn Pro Leu Lys Ser Ile Val Glu Lys Ser Ile Leu Leu Thr Glu
                          85                  90                  95

Gln Ala Leu Ala Lys Ala Gly Lys Gly Met His Gly Gly Val Pro Gly
                      100                 105                 110

Gly Lys Gln Phe Ile Glu Asn Gly Ser Glu Phe Ala Gln Lys Leu Leu
                  115                 120                 125
```

```
        Lys Lys Phe Ser Leu Leu Lys Pro Trp Ala
            130                 135

<210> SEQ ID NO 4
<211> LENGTH: 119
<212> TYPE: PRT
<213> ORGANISM: Homo sapiens
<400> SEQUENCE: 4

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
            20                  25                  30

Ser Pro Pro Glu Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu Lys Lys Phe
            100                 105                 110

Ser Leu Leu Lys Pro Trp Ala
            115

<210> SEQ ID NO 5
<211> LENGTH: 114
<212> TYPE: PRT
<213> ORGANISM: homo sapiens
<400> SEQUENCE: 5

Asp Ser Thr Gly Ala Asp Pro Ala Gln Glu Ala Gly Thr Ser Lys Pro
1               5                   10                  15

Asn Glu Glu Ile Ser Gly Pro Ala Glu Pro Ala Ser Pro Pro Glu Thr
            20                  25                  30

Thr Thr Thr Ala Gln Glu Thr Ser Ala Ala Ala Val Gln Gly Thr Ala
        35                  40                  45

Lys Val Thr Ser Ser Arg Gln Glu Leu Asn Pro Leu Lys Ser Ile Val
    50                  55                  60

Glu Lys Ser Ile Leu Leu Thr Glu Gln Ala Leu Ala Lys Ala Gly Lys
65                  70                  75                  80

Gly Met His Gly Gly Val Pro Gly Gly Lys Gln Phe Ile Glu Asn Gly
                85                  90                  95

Ser Glu Phe Ala Gln Lys Leu Leu Lys Lys Phe Ser Leu Leu Lys Pro
            100                 105                 110

Trp Ala

<210> SEQ ID NO 6
<211> LENGTH: 114
<212> TYPE: PRT
<213> ORGANISM: Homo sapiens
<400> SEQUENCE: 6

Glu Asp Ala Ser Ser Asp Ser Thr Gly Ala Asp Pro Ala Gln Glu Ala
1               5                   10                  15

Gly Thr Ser Lys Pro Asn Glu Glu Ile Ser Gly Pro Ala Glu Pro Ala
            20                  25                  30

Ser Pro Pro Glu Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
```

-continued

```
                        85                  90                  95

Phe Ile Glu Asn Gly Ser Glu Phe Ala Gln Lys Leu Leu Lys Lys Phe
                        100                 105                 110

Ser Leu

<210> SEQ ID NO 7
<211> LENGTH: 109
<212> TYPE: PRT
<213> ORGANISM: homo sapiens
<400> SEQUENCE: 7
        Glu Asp Ala Ser Ser Asp Ser Thr Gly Ala Asp Pro Ala Gln Glu Ala
        1               5                   10                  15

Gly Thr Ser Lys Pro Asn Glu Glu Ile Ser Gly Pro Ala Glu Pro Ala
                        20                  25                  30

Ser Pro Pro Glu Thr Thr Thr Thr Ala Gln Glu Thr Ser Ala Ala Ala
                        35                  40                  45

Val Gln Gly Thr Ala Lys Val Thr Ser Ser Arg Gln Glu Leu Asn Pro
                        50                  55                  60

Leu Lys Ser Ile Val Glu Lys Ser Ile Leu Leu Thr Glu Gln Ala Leu
        65                  70                  75                  80

Ala Lys Ala Gly Lys Gly Met His Gly Gly Val Pro Gly Gly Lys Gln
                        85                  90                  95

Phe Ile Glu Asn Gly Ser Glu Phe Ala Gln Lys Leu Leu
                        100                 105

<210> SEQ ID NO 8
<211> LENGTH: 104
<212> TYPE: PRT
<213> ORGANISM: homo sapiens
<400> SEQUENCE: 8
        Glu Asp Ala Ser Ser Asp Ser Thr Gly Ala Asp Pro Ala Gln Glu Ala
        1               5                   10                  15

Gly Thr Ser Lys Pro Asn Glu Glu Ile Ser Gly Pro Ala Glu Pro Ala
                        20                  25                  30

Ser Pro Pro Glu Thr Thr Thr Thr Ala Gln Glu Thr Ser Ala Ala Ala
                        35                  40                  45

Val Gln Gly Thr Ala Lys Val Thr Ser Ser Arg Gln Glu Leu Asn Pro
                        50                  55                  60

Leu Lys Ser Ile Val Glu Lys Ser Ile Leu Leu Thr Glu Gln Ala Leu
        65                  70                  75                  80

Ala Lys Ala Gly Lys Gly Met His Gly Gly Val Pro Gly Gly Lys Gln
                        85                  90                  95

Phe Ile Glu Asn Gly Ser Glu Phe
                        100

<210> SEQ ID NO 9
<211> LENGTH: 14
<212> TYPE: PRT
<213> ORGANISM: homo sapiens
<400> SEQUENCE: 9
        Asn Gly Ser Glu Phe Ala Gln Lys Leu Leu Lys Lys Phe Ser
        1               5                   10
```

In several embodiments, the peptide is represented by the amino acid sequence Ac-KQFIENGSEFAQKLLKKFS-NH$_2$ or Ac-Lys-Gln-Phe-Ile-Glu-Asn-Gly-Ser-Glu-Phe-Ala-Gln-Lys-Leu-Leu-Lys-Lys-Phe-Ser-NH$_2$, where "Ac" represents an acetyl group and the C-terminus is amidated (SEQ ID NO: 1). In some embodiments, the peptide is Lacripep™. In some embodiments, the peptide is any one or more of SEQ. IDs 1-9.

Buffers and pH

Buffers stabilize the pH of a solution, i.e., resist changes in pH when acidic or alkaline materials are added to the solution. Suitable buffers for use in the present composition include, but are not limited to, glycine hydrochloride, sodium acetate, phosphate buffered saline (PBS) (including mono- and dihydrogen phosphate salts), citrate buffer (citric acid and sodium citrate), phosphate-citrate buffer, tris(hydroxymethyl)aminomethane (Tris), carbonate buffers (sodium carbonate and sodium bicarbonate), borate buffers, and combinations thereof.

In some embodiments, the buffer comprises one or more of sodium acetate, phosphate buffered saline (PBS), citrate buffer (citric acid and sodium citrate), and phosphate-citrate buffer. In some embodiments, the buffer is selected from the group consisting of sodium acetate, phosphate buffered saline (PBS), citrate buffer (citric acid and sodium citrate), and phosphate-citrate buffer.

In some embodiments, the amount of buffer is limited to less than 0.1, 0.2, 0.3, or, 0.4%, or within a range defined by any two of the preceding values.

In an embodiment, the buffer is a citrate buffer (citric acid and sodium citrate). In an embodiment, the only buffer is a citrate buffer, and no other buffering agent is present in the composition.

In some embodiments the pH of the composition is between 6 to 7.4; 6.1 to 7.3; 6.2 to 7.2; 6.3 to 7.1; 6.4 to 7.0; 6.5 to 6.9; 6.6 to 6.8; or any pH in between.

In some embodiments the pH of the composition is, or is about, 6; 6.1; 6.2; 6.3; 6.4; 6.5; 6.6; 6.7; 6.8; 6.9; 7; 7.1; 7.2; 7.3; 7.4, or a range defined by any two of the preceding values.

In an embodiment, the pH of the composition is, or is about, 6.2, 6.3, 6.4, 6.5, 6.6, 6.7, or 6.8.

The pH of the composition can be adjusted as necessary by the addition of solutions of an acid or a base. Any acid or base whose conjugate is ophthalmically acceptable may be used. Acids include for example hydrochloric acid, bases include for example sodium and potassium hydroxides.

Chelating Agents

In some embodiments, the composition further comprises one or more chelating agents. In some embodiments, the chelating agents are selected from the group consisting of ethylenediaminetetraacetic acid, edetate disodium (EDTA), ethylenediamine, amino acids such as glutamic acid and histidine, organic diacids such as oxalic acid, malonic acid, succinic acid, and the like, 3-dimercaptopropanesulfonic acid (DMPS), alpha lipoic acid (ALA), 2,3-dimercaptopropanesulfonic acid (DMPS), thiamine tetrahydrofurfuryl disulfide (TTFD), penicillamine, dimercaptosuccinic acid (DMSA), combinations thereof, and pharmaceutically acceptable salts of the foregoing.

In some embodiments, the chelating agent, as a non-limiting example EDTA, or a pharmaceutically acceptable salt thereof, is present at between 0.0001% and 0.1%; between 0.0005% and 0.05%; 0.0006% and 0.04%; 0.0007% and 0.003%; 0.0008% and 0.002%; 0.0009% and 0.001%; or any value contained therein or ranges therein. In some embodiments, the chelating agent is present at an amount that is, or is less than, 0.1%; 0.09%; 0.08%; 0.07%; 0.06%; 0.05%; 0.04%; 0.03%; 0.02%; 0.01%; 0.009%; 0.008%;
0.007%; 0.006%; 0.005%; 0.004%; 0.003%; 0.002%; 0.001%; 0.0009%; 0.0008%; 0.0007%; 0.0006%; 0.0005%; 0.0004%; 0.0003%; 0.0002%; or 0.0001%, or is within a range defined by any two of the preceding values.

In some embodiments, the chelating agent, such as EDTA or others, or a pharmaceutically acceptable salt thereof, is present at less than about 0.05% or less than about 0.005% (e.g., at about 0.001%).

Stabilizing Agents

Buffers and chelators can stabilize peptide ingredients of compositions by maintaining pH and reducing metal ion mediated degradation of the peptides. In some embodiments, the composition further comprises one or more peptide stabilizing agents in addition to a buffer and/or a chelating agent. In some embodiments, the one or more stabilizing agents in addition to a buffer and/or chelating agent are selected from the group consisting of disaccharides, polysaccharides (e.g., hyaluronic acid), polyols, sugar alcohols, amino acids, proteins (e.g., serum albumin), and combinations thereof. In some embodiments, non-limiting examples of stabilizers include trehalose, sucrose, mannitol, sorbitol, polysorbate 20, polysorbate 80, histidine, glycine, and arginine, and combinations thereof. In an embodiment the composition does not include a stabilizer in addition to a buffering agent and/or a chelator.

Polypeptide Degradation

Polypeptides are prone to physical and chemical degradation, for example, aggregation, shearing, oxidation, deamidation, and hydrolysis. Indeed, liquid peptide compositions have a high risk for physical and chemical instability during manufacturing and storage. Reducing polypeptide degradation is particularly important for dilute peptide formulations, which initially contain very small amounts of a particular peptide. Loss of even miniscule amounts of the initial small amount can significantly impact the efficacy of the composition.

In some embodiments, composition stability is determined by high-performance liquid chromatography (HPLC). In some embodiments, composition stability is determined by high-performance liquid chromatography-mass spectrometry (HPLC-MS).

In some embodiments, composition stability is determined after a sealed container of the composition has been in the dark, or exposed to light, at room temperature for days, weeks or months (e.g., 1-24 days or months, e.g., 1, 2, 3, 4, 5, 6, 7, 8, 9, 10, 11, 12, 13, 14, 15, 16, 17, 18, 19, 20, 21, 22, 23, 24 days or months).

In some embodiments, composition stability is determined after a sealed container of the composition has been in the dark, or exposed to light, at 2 to 8° C., for example 5° C., or any value in between, for days, weeks or months, (e.g., 1-24 days or months, e.g., 1, 2, 3, 4, 5, 6, 7, 8, 9, 10, 11, 12, 13, 14, 15, 16, 17, 18, 19, 20, 21, 22, 23, 24 days or months)

In some embodiments, composition stability is determined after a sealed container of the composition has been in the dark, or exposed to light, at −10 to −30° C., for example −25° C., or any value in between, for days, weeks or months, (e.g., 1-24 days or months, e.g., 1, 2, 3, 4, 5, 6, 7, 8, 9, 10, 11, 12, 13, 14, 15, 16, 17, 18, 19, 20, 21, 22, 23, 24 days or months)

In some embodiments, composition stability is determined after a sealed container of the composition has been in the dark, or exposed to light, and moved from 2 to 8° C. (storage), or any value in between, to room temperature for 5 minutes, either one, two, or three times per day, for 1-60 days.

In some embodiments, the composition provides at least 99.99%, 99.95%, 99.9%, 99%; 98%; 97%; 96%; 95%; 94%; 93%; 92%; 91%; 90%; 89%; 88%; 87%; 86%; 85%; 84%; 83%; 82%; 81%; 80%; 79%; 78%; 77%; 76%; 75%; 74%; 73%; 72%; 71%; 70%; or any value in between, of the original amount or activity of the polypeptide, or a pharmaceutically acceptable salt thereof, in an intact, non-degraded or non-aggregated form, following exposure to one or more of the conditions described above and herein. In a one embodiment, the amount or activity of the intact polypeptide, or a pharmaceutically acceptable salt thereof, is at least 80%, 85%, 90% or 95% of the original amount. In some embodiments, the amount or activity of intact polypeptide, or a pharmaceutically acceptable salt thereof, is at least 97% of the original amount.

In some embodiments, the composition comprises not more than 30%; 29%; 28%; 27%; 26%; 25%; 24%; 23%; 22%; 21%; 20%; 19%; 18%; 17%; 16%; 15%; 14%; 13%; 12%; 11%; 10%; 9%; 8%; 7%; 6%; 5%; 4%; 3%; 2%; 1%; of a peptide aggregation product or peptide degradation product, or is within a range defined by any two of the preceding values, following exposure to one or more of the conditions described above and herein. In some embodiments, the composition comprises not more than about 15%, or not more than 20%, inactive peptide.

In some embodiments, the composition comprises not more than 30%; 29%; 28%; 27%; 26%; 25%; 24%; 23%; 22%; 21%; 20%; 19%; 18%; 17%; 16%; 15%; 14%; 13%; 12%; 11%; 10%; 9%; 8%; 7%; 6%; 5%; 4%; 3%; 2%; 1%; of the total amounts of peptide degradation products and peptide aggregation products, or is within a range defined by any two of the preceding values, following exposure to one or more of the conditions described above and herein.

In some embodiments, the composition comprises very low levels of buffer, in combination with very low levels of a chelator. In some embodiments, the buffer is a citrate buffer and the chelator is EDTA. The combination of low levels of citrate buffer (e.g., 0.012% to 0.020%) and EDTA (e.g., 0.0005% to 0.005%), provide the surprising and unexpected benefit of stabilizing compositions containing low levels of a peptide (e.g., 0.001 to 0.01%). Such stabilized compositions provide advantages in manufacturing, transportation, storage, and use of the peptide compositions by decreasing peptide aggregation and degradation, thus maintaining the efficacy of peptide compositions and reducing buildup of undesired breakdown products in the composition.

In some embodiments, the stabilized composition reduces the rate of formation of breakdown and/or aggregation products.

In some embodiments, the peptide is Lacripep™. In some embodiments, the stabilized composition comprises less than about 5%, 4%, 3%, 2%, or about 1% total degradation products. In some embodiments, the stabilized composition comprises not more than 0.25%, 0.5%, 0.75%, 1.0%, 1.25%, 1.5%, 1.75%, or 2.0% of any single degradation product. In some embodiments, the stabilized composition comprises less than about 5%, 4%, 3%, 2%, or about 1% total degradation products and not more than 0.25%, 0.5%, 0.75%, 1.0%, 1.25%, 1.5%, 1.75%, or 2.0% of any single degradation product.

In some embodiments, the aggregation products include dimers, trimers, tetramers, or larger-order peptide aggregates.

Preservatives

In some embodiments, the composition further comprises one or more preservatives to prevent the growth of microbes in the composition. In some embodiments, the composition further comprises one or more preservatives to maintain the sterility of the composition. In some embodiments, the composition further comprises one or more preservatives to prevent the growth of microbes and maintain the sterility of the composition. However, in many embodiments, the preservative is provided in reduced amounts. In some embodiments, the one or more preservatives are selected from the group consisting of benzalkonium chloride, cetylpyridinium chloride, chlorobutanol, benzododecinium bromide, methylparaben, propylparaben, phenylethyl alcohol, sodium perborate, edentate disodium, chlorobutanol, sorbic acid, benzethonium chloride, sodium acetate, polyquaternium-1, phenylmercuric nitrate, phenylmercury borate, sodium propionate, chlorhexidine, thimerosal, and combinations thereof. In some embodiments, the composition does not contain a preservative. In some embodiments, the composition does not contain detectable levels of a preservative. In some embodiments, the polypeptide can be self-preserving, i.e., no additional preservatives are necessary to maintain sterility of the composition.

In some embodiments, the preservative is present at between 0.0001% and 1%; between 0.01% and 0.9%; 0.05% and 0.8%; 0.1% and 0.7%; 0.2% and 0.3%; 0.4% or 0.5%, or any value contained therein. In some embodiments, the preservative is present in an amount that is, or is less than, 1%; 0.9%; 0.8%; 0.7%; 0.6%; 0.5%; 0.4%; 0.3%; 0.2%; 0.1%; 0.09%; 0.08%; 0.07%; 0.06%; 0.05%; 0.04%; 0.03%; 0.02%; 0.01%; 0.009%; 0.008%; 0.007%; 0.006%; 0.005%; 0.004%; 0.003%; 0.002%; or 0.001%, or is within a range defined by any two of the preceding values.

In some embodiments, the composition is sterile. In some embodiments, the composition is manufactured from sterile ingredients in an aseptic environment. In some embodiments, the composition is sterilized just prior to packaging. In some embodiments, the composition is sterilized by one or more of the following (1) addition of one or more quaternary ammonium chlorides to the composition; (2) exposing the composition to ionizing radiation; (3) filtering the composition; (4) exposing the composition to ionizing radiation after packaging; and any combination of the foregoing. In some embodiments, filtering comprises passing the composition through a filter (including but not limited to a 0.22 micron filter with a polyvinyldifluoride or other suitable membrane (e.g., polyethersulfone).

In some embodiments, the peptide is provided in a bacteriostatic and/or bactericidal amount. In some embodiments, the amount of peptide provided in the composition is bacteriostatic and/or bactericidal when one, two or three drops of the composition are administered to the surface of the eye. In some embodiments, the peptide is bacteriostatic and/or bactericidal for Gram-positive and/or Gram-negative bacteria, for example, when administered to the eye. In some embodiments the amount of peptide in the composition is sufficient to inhibit bacterial growth by at least 20%, 30%, 40%, 50%, 60%, 70%, 80% or 90% relative to a control composition not containing the peptide in a standard bacteriological assay. In some embodiments, the bacteria in the bacteriological assay are selected from P. aeruginoa, E. coli, S. epidermis, S. aureus, or combinations thereof. In some embodiments, the bacteriological assay is selected from a bacterial growth assay, SYTOX Green assay, a well diffusion assay, a broth or agar dilution assay, a time-kill test, antimicrobial gradient assay, a ATP-bioluminescence assay, or a propidium-iodide flow cytometry assay. In some embodiments, the peptide provided in a bacteriostatic and/or bactericidal amount is Lacripep™.

In some embodiments, the bacteriological assay is a USP Section <51> assay or FDA-mandated assay. For example, the original product containers, containing the peptide solution, and inoculate each container with one of the prepared and standardized inoculums (e.g., P. aeruginoa, E. coli, S. epidermis, S. aureus, or combinations thereof) and mix. The volume of the suspension inoculums should be about 0.5% to 1.0% of the volume of the product, and the concentration of the test preparation immediately after inoculation is between $1 \times 10^5$ and $1 \times 10^6$ colony forming organisms (CFU) per mL of product (as measured by, for example, the plate count method, or another microbial enumeration test).

The inoculated containers are incubated at between 22.5±2.5° C. in a controlled environment and sampled at specified intervals, for example, 7, 14, and 28 days. Any change in appearance is recorded, and the CFU/mL are determined, at each sampling. The change in $\log_{10}$ values of CFU/mL provides the change over time in terms of log reductions. The product provides not less than 1.0 log reduction from the initial calculated count at 7 days, not less than 3.0 log reduction from the initial count at 14 days, and no increase from the 14 day count at 28 days for bacteria, and no increase from the initial count of yeast and molds. In some embodiments, the peptide provided in a bacteriostatic and/or bactericidal amount is Lacripep™.

Surfactants

In some embodiments, the composition further comprises one or more surfactants. In some embodiments, the one or more surfactants are selected from detergents, wetting agents, emulsifiers, foaming agents, dispersants, and combinations thereof.

In some embodiments, the surfactant is an anionic surfactant. Anionic surfactants contain anionic functional groups at their head, such as sulfate, sulfonate, phosphate, and carboxylates. In some embodiments, the surfactant is a sulfate, sulfonate, or phosphate ester, e.g., a sulfate ester. In some embodiments, the surfactant is selected from the group comprising or consisting of ammonium lauryl sulfate and sodium lauryl sulfate, e.g., sodium lauryl sulfate (also called SDS, sodium dodecyl sulfate). In some embodiments, the surfactant is an alkyl-ether sulfate, such as selected from the group comprising or consisting of sodium laureth sulfate (also known as sodium lauryl ether sulfate), and sodium myreth sulfate. In some embodiments, the surfactant is a docusate, such as dioctyl sodium sulfosuccinate, perfluorooctanesulfonate (PFOS), perfluorobutanesulfonate, linear alkylbenzene sulfonates (LABs). In some embodiments, the surfactant is a carboxylate, such as alkyl carboxylates (soaps), for instance sodium stearate; sodium lauroyl sarcosinate and carboxylate-based fluorosurfactants such as perfluorononanoate, perfluorooctanoate (PFOA or PFO). In some embodiments, the polypeptide contributes to the surfactant properties of the composition.

In some embodiments, the surfactant is a cationic surfactant, of which the charge can be pH dependent, such as primary, secondary or tertiary amines, for instance octenidine dihydrochloride; or may comprise permanently charged quaternary ammonium cations, such as alkyltrimethylammonium salts, for instance cetyl trimethylammonium bromide (CTAB) or cetyl trimethylammonium chloride (CTAC); cetylpyridinium chloride (CPC); benzalkonium chloride (BAC); benzethonium chloride (BZT); 5-Bromo-5-nitro-1,3-dioxane; dimethyldioctadecylammonium chloride; or dioctadecyldimethylammonium bromide (DODAB). In some embodiments, the surfactant is a zwitterionic surfactant (i.e. having both cationic and anionic centers attached to the same molecule). The cationic part may be based on primary, secondary, or tertiary amines or quaternary ammonium cations. The anionic part can be more variable and include sulfonates, as in CHAPS (3-[(3-Cholamidopropyl)dimethylammonio]-1-propanesulfonate). Other anionic groups are sultaines illustrated by cocamidopropyl hydroxysultaine; betaines, e.g., cocamidopropyl betaine; phosphates, e.g. lecithin. In some embodiments, the surfactant may be a non-ionic surfactant (not charged).

Many long chain alcohols exhibit some surfactant properties, and are provided herein as part of a composition in some embodiments. Prominent among these are the fatty alcohols cetyl alcohol, stearyl alcohol, and cetostearyl alcohol (consisting predominantly of cetyl and stearyl alcohols), and oleyl alcohol. Other surfactants include cocamide MEA, cocamide DEA, dodecyldimethylamine oxide, and polyethoxylated tallow amine (POEA). Examples of non-ionic surfactants include polyoxyethylene glycol alkyl ethers, such as octaethylene glycol monododecyl ether or pentaethylene glycol monododecyl ether; polyoxypropylene glycol alkyl ethers; glucoside alkyl ethers, such as decyl glucoside, lauryl glucoside, or octyl glucoside; polyoxyethylene glycol octylphenol ethers, such as Triton X-100; polyoxyethylene glycol alkylphenol ethers, such as Nonoxynol-9; glycerol alkyl esters, such as glyceryl laurate; polyoxyethylene glycol sorbitan alkyl esters (polysorbate); sorbitan alkyl esters (Spans); block copolymers of polyethylene glycol and polypropylene glycol, or Poloxamers.

In some embodiments, the composition may contain one or more ingredients found in artificial tears in amounts known in the art, including but not limited to: carboxymethyl cellulose, polyvinyl alcohol, hydroxypropyl methylcellulose (a.k.a. HPMC or hypromellose), hydroxypropyl cellulose, hydroxyethyl cellulose (HEC), and hyaluronic acid (a.k.a. hyaluronan, HA), and combinations thereof. In some embodiments, the composition does not contain any of the preceding artificial tear ingredients.

In some embodiments, the surfactant is another peptide or protein. In some embodiments, as a non-limiting example, the surfactant is human serum albumin. In some embodiments, as another non-limiting example, the surfactant is Lacripep™.

In several embodiments, the surfactant is tyloxapol (formaldehyde;oxirane;4-(2,4,4-trimethylpentan-2-yl)phenol). In an embodiment, the only surfactant is tyloxapol, and no other surfactant agent is present in the composition.

In some embodiments, the surfactant, as a non-limiting example tyloxapol, is present at between 0.01% and 1%; between 0.05% and 0.9%; 0.1% and 0.8%; 0.2% and 0.7%; 0.3% and 0.6%; 0.4% or 0.5%, or any value contained therein. In some embodiments, the surfactant is present in an amount that is, or is less than, 1%; 0.9%; 0.8%; 0.7%; 0.6%; 0.5%; 0.4%; 0.3%; 0.2%; 0.1%; 0.09%; 0.08%; 0.07%; 0.06%; 0.05%; 0.04%; 0.03%; 0.02%; 0.01%; 0.009%;

0.008%; 0.007%; 0.006%; 0.005%; 0.004%; 0.003%; 0.002%; or 0.001%, or is within a range defined by any two of the preceding values.

In some embodiments, the composition does not contain a surfactant. In some embodiments, the composition does not contain detectable levels of a surfactant.

Tonicity Agents and Osmolality

In some embodiments, the composition further comprises one or more tonicity agents. Such tonicity agents are in addition to any polypeptide or buffer that has tonicity-modifying effects. In some embodiments, the one or more tonicity agents are selected from propylene glycol, polyethylene glycols, sodium chloride, potassium chloride, magnesium chloride, calcium chloride, simple sugars such as dextrose, fructose, galactose, and/or simple polyols such as the sugar alcohols mannitol, sorbitol, xylitol, lactitol, isomaltitol, maltitol, hydrogenated starch hydrolysates, glycerin, and combinations thereof.

In some embodiments, the one or more tonicity agents are selected from sodium chloride, potassium chloride, magnesium chloride, calcium chloride, dextrose, mannitol, and combinations thereof.

In some embodiments, the tonicity agent is sodium chloride. In some embodiments, the sodium chloride is present at between 0.01% and 1%; between 0.05% and 0.9%; 0.1% and 0.8%; 0.2% and 0.75%; 0.3% and 0.7%; 0.4% and 0.6%; or any value contained therein. In some embodiments, the sodium chloride is present at an amount that is, or is about, 1%; 0.95%; 0.9%; 0.85%; 0.8%; 0.75%; 0.7%; 0.65%; 0.6%; 0.55%; 0.5%; 0.45%; 0.4%; 0.35%; 0.3%; 0.25%; 0.2%; 0.15%; 0.1%; 0.09%; 0.08%; 0.07%; 0.06%; 0.05%; 0.04%; 0.03%; 0.02%; or 0.01%; or is within a range defined by any two of the preceding values.

In some embodiments, the only tonicity agent is sodium chloride, and no other tonicity agent is present in the composition.

In some embodiments, a tonicity agent, as a non-limiting example sodium chloride, is added to the composition to adjust the osmolality to a desired level. In some embodiments, the osmolality of the composition is about 150 to about 400 mOsm/kg; about 170 to about 380 mOsm/kg; about 190 to about 360 mOsm/kg; about 210 to about 340 mOsm/kg; about 230 to about 320 mOsm/kg; about 250 to about 300 mOsm/kg; about 270 to about 280 mOsm/kg; or any value in between. In some embodiments, the osmolality of the composition is about 250 to about 350 mOsm/kg; about 260 to about 340 mOsm/kg; about 270 to about 330 mOsm/kg; about 280 to about 320 mOsm/kg; about 290 to about 310 mOsm/kg; or any value in between.

In some embodiments, the osmolality of the composition is, or is about, 150 mOsm/kg; 160 mOsm/kg; 170 mOsm/kg; 180 mOsm/kg; 190 mOsm/kg; 200 mOsm/kg; 210 mOsm/kg; 220 mOsm/kg; 230 mOsm/kg; 240 mOsm/kg; 250 mOsm/kg; 260 mOsm/kg; 270 mOsm/kg; 280 mOsm/kg; 290 mOsm/kg; 300 mOsm/kg; 310 mOsm/kg; 320 mOsm/kg; 330 mOsm/kg; 340 mOsm/kg; or 350 mOsm/kg, or is within a range defined by any two of the preceding values In some embodiments, the osmolality of the composition is between about 280 mOsm/kg and about 320 mOsm/kg. In one embodiment, the osmolality of the composition is about 300 mOsm/kg. In some embodiments, NaCl is used to adjust the osmolality of the solution to the desired level. In an embodiment, the composition is, or is about, isotonic with human tears.

Polypeptides and Other Ingredients

In some embodiments, the polypeptide, or a pharmaceutically acceptable salt thereof, has between 10 to 150 amino acids; between 10 to 50 amino acids; between 100 to 150 amino acids; between 30 to 70 amino acids; or any number contained therein. In some embodiments, the polypeptide, or a pharmaceutically acceptable salt thereof, has between 10 to 30 amino acids; 11 to 29 amino acids; 12 to 28 amino acids; 13 to 27 amino acids; 14 to 26 amino acids; 15 to 25 amino acids; 16 to 24 amino acids; 17 to 23 amino acids; 18 to 22 amino acids; 19 to 21 amino acids; or any number contained therein. In some embodiments, the polypeptide, or a pharmaceutically acceptable salt thereof, is, or is about, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length, or a range defined by any two of the preceding values.

In some embodiments, the C-terminus of the polypeptide, or a pharmaceutically acceptable salt thereof, is amidated. In some embodiments, the N-terminus of the polypeptide, or a pharmaceutically acceptable salt thereof, is acetylated. In some embodiments, one or more side chains of the polypeptide, or a pharmaceutically acceptable salt thereof, are acetylated. In some embodiments, one or more side chains of the polypeptide, or a pharmaceutically acceptable salt thereof, are amidated. In some embodiments, the N-terminus of the polypeptide, or a pharmaceutically acceptable salt thereof, is acetylated and the C-terminus of the polypeptide, or a pharmaceutically acceptable salt thereof, is amidated.

In some embodiments, the polypeptide, or a pharmaceutically acceptable salt thereof, comprises, consists or consists essentially of the amino acid sequence: Ac-Lys-Gln-Phe-Ile-Glu-Asn-Gly-Ser-Glu-Phe-Ala-Gln-Lys-Leu-Leu-Lys-Lys-Phe-Ser-Leu-Leu-Lys-Pro-Trp-Ala-NH$_2$ (SEQ ID NO: 2), where "Ac" represents an acetyl group and the C-terminus is amidated (indicated by "NH$_2$"). In some embodiments, the polypeptide, or a pharmaceutically acceptable salt thereof, comprises the amino acid sequence: Ac-Lys-Gln-Phe-Ile-Glu-Asn-Gly-Ser-Glu-Phe-Ala-Gln-Lys-Leu-Leu-Lys-Lys-Phe-Ser-NH$_2$ (SEQ ID NO: 1), where "Ac" represents an acetyl group and the C-terminus is amidated (indicated by "NH$_2$"). In some embodiments, the polypeptide, or a pharmaceutically acceptable salt thereof, comprises, consists, or consists essentially of a sequence selected from the group of SEQ ID NOs: 3-9, or fragments, or pharmaceutically acceptable salts thereof.

In some embodiments, the amount of polypeptide, or a pharmaceutically acceptable salt thereof, in the composition is, or is about, 0.0001% to 1%; 0.0005% to 0.5%; 0.001% to 0.1%; 0.005% to 0.05%; 0.006% to 0.04%; 0.007% to 0.03%; 0.008% to 0.02%; or 0.009% to 0.01%. In an embodiment, the polypeptide, or a pharmaceutically acceptable salt thereof, is present in the composition at about 0.003% to 0.09% (e.g., 0.005%, 0.01%, 0.02%, 0.03% and ranges thereof).

In some embodiments, the polypeptide, or a pharmaceutically acceptable salt thereof, is present in the composition in an amount that is, is about, is more than, or is less than, 0.0001, 0.00025, 0.0005, 0.00075, 0.001, 0.002, 0.003, 0.004, 0.005, 0.006, 0.007, 0.008, 0.009, 0.010, 0.011, 0.012, 0.013, 0.014, 0.015, 0.020, 0.030, 0.040, 0.050, 0.060, 0.070, 0.080, 0.090, 0.10, 0.20, 0.30, 0.40, 0.50, 0.60, 0.70, 0.80, 0.90, or 1.0%, or a range defined by any two of the preceding values.

In some embodiments, the composition is a sterile aqueous composition comprising, consisting or consisting essentially of about 0.001% to about 0.05% of a polypeptide, such as Lacripep™ or the other peptides identified herein, or a pharmaceutically acceptable salt thereof; about 0.001% to about 0.015% anhydrous citric acid; about 0.02% to about 0.40% sodium citrate dihydrate; about 0.0005% to about 0.005% disodium EDTA; about 0.005% to about 0.15% tyloxapol, and optionally, about 0.005% to about 0.1% methylparaben; wherein the pH of the composition is adjusted using NaOH or HCl to be about 6.2 pH to about 6.8 pH, and the osmolality of the composition is adjusted using NaCl to be between about 250 to about 350 mOsm/kg. In some embodiments, the amount of NaCl is about 0.1% to about 1%. In an embodiment, the composition does not include methylparaben. In an embodiment, the composition consists of only the listed ingredients, and does not contain any additional active ingredients, excipients (e.g., viscosity building agents, buffering agents, chelating agents, stabilizing agents, preservatives, surfactants, and tonicity agents), carriers or diluents.

In some embodiments, the composition is a sterile aqueous composition comprising, consisting or consisting essentially of about 0.01%±0.001% of a polypeptide, such as Lacripep™ or the other peptides identified herein, or a pharmaceutically acceptable salt thereof; about 0.0098%±0.001% anhydrous citric acid; about 0.279%±0.028% sodium citrate dihydrate; about 0.001%±0.0001% disodium EDTA; about 0.05%±0.005% tyloxapol, about 0.04%±0.004% methylparaben; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%. In an embodiment, the composition does not include methylparaben.

In some embodiments, the composition is a sterile aqueous composition comprising, consisting or consisting essentially of about 0.005%±0.0005% of a polypeptide, such as Lacripep™ or the other peptides identified herein, or a pharmaceutically acceptable salt thereof; about 0.0098%±0.001% anhydrous citric acid; about 0.279%±0.028% sodium citrate dihydrate; about 0.001%±0.0001% disodium EDTA; about 0.05%±0.005% tyloxapol, about 0.04%±0.004% methylparaben; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%. In an embodiment, the composition does not include methylparaben.

In some embodiments, the composition is a sterile aqueous composition comprising about 0.001%±0.0001% of a polypeptide, such Lacripep™ or the other peptides identified herein, or a pharmaceutically acceptable salt thereof; about 0.0098%±0.001% anhydrous citric acid; about 0.279%±0.028% sodium citrate dihydrate; about 0.001%±0.0001% disodium EDTA; about 0.05%±0.005% tyloxapol, about 0.04%±0.004% methylparaben; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%. In an embodiment, the composition does not include methylparaben.

In some embodiments, including but not limited to the sterile compositions above, the polypeptide is Lacripep™, having SEQ ID NO: 1, or a pharmaceutically acceptable salt thereof. In some embodiments the polypeptide is a polypeptide having SEQ ID NO: 2, or a pharmaceutically acceptable salt thereof. In some embodiments the polypeptide is a polypeptide having a sequence selected from the group of SEQ ID NOs:3-9, or a pharmaceutically acceptable salt or fragment or fragments thereof.

In some embodiments, including but not limited to the sterile compositions above, the pH of the composition is between about 6.5 to about 6.6.

In some embodiments, including but not limited to the sterile compositions above, the osmolality of the composition is between about 280 to about 320 mOsm/kg. In some embodiments, the osmolality of the composition is about 300 mOsm/kg.

In some embodiments, the composition is a sterile aqueous composition comprising about 0.01%±0.001% Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

In some embodiments, the composition is a sterile aqueous composition comprising about 0.005%±0.0005% Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

In some embodiments, the composition is a sterile aqueous composition comprising about 0.001%±0.0001% Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

In an embodiment, including but not limited to the sterile compositions above, the composition consists of only the listed ingredients, and does not contain any additional active ingredients, excipients (e.g., viscosity building agents, buffering agents, chelating agents, stabilizing agents, preservatives, surfactants, and tonicity agents), carriers or diluents. In some embodiments, the amounts of any one or more of the listed ingredients is provided in an amount that is ±5%, and/or ±1% of the listed amount.

In some embodiments, the compositions disclosed herein are prepared as a solution, gel or ointment. Gels or ointments are advantageous in providing the composition in contact with the eye for a longer period of time than a solution or provide other benefits. Therefore, in one embodiment, a gel or ointment is useful when applying the composition to the subject when the subject will be sleeping, or when the subject's eyes will be closed for an extended period of time (e.g., 1, 2, 3, 4, 5 or more hours). Gels or ointments may be used at other times based on user preference.

Non-limiting exemplary compositions, (which can be used in the methods and kits disclosed herein), include the following compositions in Tables 1.1, 1.2, 1.3 and 1.4.

TABLE 1.1

| Component (% w/w) | A | B | C | D | E |
|---|---|---|---|---|---|
| Lacripep ™ (SEQ ID NO. 1) | 0.01 | 0.01 | 0.01 | 0.01 | 0.01 |
| Citric Acid (Anhydrous) | 0.0098 | 0.0098 | 0.0098 | 0.0098 | 0.0098 |
| Sodium Citrate (Dihydrate) | 0.279 | 0.279 | 0.279 | 0.279 | 0.279 |
| EDTA Disodium | 0.001 | 0 | 0.001 | 0 | 0.001 |
| Tyloxapol | 0.05 | 0.05 | 0 | 0 | 0.05 |
| Methylparaben | 0 | 0 | 0 | 0 | 0.04 |
| 10% NaOH (aq) or 10% HCl (aq) | Adjust pH to 6.5 ± 0.3 | Adjust pH to 6.5 ± 0.3 | Adjust pH to 6.5 ± 0.3 | Adjust pH to 6.5 ± 0.3 | Adjust pH to 6.5 ± 0.3 |
| 25% NaCl Solution | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg |
| Sterile Purified Water | qs ad 100 | qs ad 100 | qs ad 100 | qs ad 100 | qs ad 100 |

TABLE 1.2

| Component (% w/w) | F | G | H | I | J |
|---|---|---|---|---|---|
| Lacripep ™ (SEQ ID NO. 1) | 0.005 | 0.005 | 0.005 | 0.005 | 0.005 |
| Citric Acid (Anhydrous) | 0.0098 | 0.0098 | 0.0098 | 0.0098 | 0.0098 |
| Sodium Citrate (Dihydrate) | 0.279 | 0.279 | 0.279 | 0.279 | 0.279 |
| EDTA Disodium | 0.001 | 0 | 0.001 | 0 | 0.001 |
| Tyloxapol | 0.05 | 0.05 | 0 | 0 | 0.05 |
| Methylparaben | 0 | 0 | 0 | 0 | 0.04 |
| 10% NaOH (aq) or 10% HCl (aq) | Adjust pH to 6.5 ± 0.3 | Adjust pH to 6.5 ± 0.3 | Adjust pH to 6.5 ± 0.3 | Adjust pH to 6.5 ± 0.3 | Adjust pH to 6.5 ± 0.3 |
| 25% NaCl Solution | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg |
| Sterile Purified Water | qs ad 100 | qs ad 100 | qs ad 100 | qs ad 100 | qs ad 100 |

TABLE 1.3

| Component (% w/w) | K | L | M | N | O |
|---|---|---|---|---|---|
| Lacripep ™ (SEQ ID NO. 1) | 0.001 | 0.001 | 0.001 | 0.001 | 0.001 |
| Citric Acid (Anhydrous) | 0.0098 | 0.0098 | 0.0098 | 0.0098 | 0.0098 |
| Sodium Citrate (Dihydrate) | 0.279 | 0.279 | 0.279 | 0.279 | 0.279 |
| EDTA Disodium | 0.001 | 0 | 0.001 | 0 | 0.001 |
| Tyloxapol | 0.05 | 0.05 | 0 | 0 | 0.05 |
| Methylparaben | 0 | 0 | 0 | 0 | 0.04 |
| 10% NaOH (aq) or 10% HCl (aq) | Adjust pH to 6.5 ± 0.3 | Adjust pH to 6.5 ± 0.3 | Adjust pH to 6.5 ± 0.3 | Adjust pH to 6.5 ± 0.3 | Adjust pH to 6.5 ± 0.3 |
| 25% NaCl Solution | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg |
| Sterile Purified Water | qs ad 100 | qs ad 100 | qs ad 100 | qs ad 100 | qs ad 100 |

TABLE 1.4

| Component (% w/w) | P | Q | R | S | T |
|---|---|---|---|---|---|
| Lacripep ™ (SEQ ID NO. 1) | 0.0001 | 0.0001 | 0.0001 | 0.0001 | 0.0001 |
| Citric Acid (Anhydrous) | 0.0098 | 0.0098 | 0.0098 | 0.0098 | 0.0098 |
| Sodium Citrate (Dihydrate) | 0.279 | 0.279 | 0.279 | 0.279 | 0.279 |
| EDTA Disodium | 0.001 | 0 | 0.001 | 0 | 0.001 |
| Tyloxapol | 0.05 | 0.05 | 0 | 0 | 0.05 |
| Methylparaben | 0 | 0 | 0 | 0 | 0.04 |
| 10% NaOH (aq) or 10% HCl (aq) | Adjust pH to 6.5 ± 0.3 | Adjust pH to 6.5 ± 0.3 | Adjust pH to 6.5 ± 0.3 | Adjust pH to 6.5 ± 0.3 | Adjust pH to 6.5 ± 0.3 |
| 25% NaCl Solution | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg | Qs ad Osmolality to 300 ± 20 mOsm/kg |
| Sterile Purified Water | qs ad 100 | qs ad 100 | qs ad 100 | qs ad 100 | qs ad 100 |

Embodiments of the compositions of Tables 1.1-1.4 also include compositions with the amounts of the disclosed ingredients in a range of ±1% of the disclosed amount, in a range of ±2% of the disclosed amount, in a range of ±3% of the disclosed amount, in a range of ±4% of the disclosed amount, or in a range of ±5% of the disclosed amount. In some embodiments, compositions of Tables 1.1-1.4 maintains at least about 99.0%, 99.9%, 99.95%, or 99.99% of the Lacripep polypeptide of SEQ ID NO: 1 in its initial, undegraded form in the composition after storage of the composition for at least 1 or 2 weeks, 1, 2, 3, 4 or 5 months at −20±5° C., 5±3° C. or 25±2° C. and 25±5% relative humidity. In some embodiments, compositions of Tables 1.1-1.4 maintains at least about 80% or 90% of the Lacripep polypeptide of SEQ ID NO: 1 in its initial, undegraded form in the composition after storage of the composition for at least 12 months at −20±5° C. or 5±3° C. In some embodiments, the compositions of Tables 1.1-1.4 contain about 0.2-0.8%, or about 0.5% NaCl.

Other Therapeutic Ingredients

In some embodiments the compositions include one or more additional therapeutic agents in addition to the polypeptides disclosed herein. These therapeutic agents can include substances known to those skilled in the art for the treatment of dry eye and related syndromes and conditions, including Sjogren's Syndrome. The additional therapeutic ingredients can treat the disease, syndrome or condition, or can relieve symptoms associated with the disease, syndrome or condition. A non-exhaustive list of additional therapeutic agents includes: cholinergics (e.g., pilocarpine, cevimeline), Cyclosporine, Lifitegrast, Dexamethasone (or other corticosteroids such as prednisolone), Hyaluronic acid (and its derivatives) with or without chondroitin sulfate, Cyclokat, SI-614, skQl, Cis-UCA, CycloASol, RGN-259, Diquafosol, Anakinra, Tofacitinib, EBI-005, EGP-437, KP-121, MIM-D3, OTX-DP, rebamipide (OPC-12759), and RU-101. In some embodiments, the additional therapeutic agent is Xiidra (lifitegrast, SAR-1118). In some embodiments, the one or more additional therapeutic agents are provided as a salt of the polypeptide. Artificial tears and other lubricants that contain one or more of carboxymethyl cellulose, polyvinyl alcohol, hydroxypropyl methylcellulose (a.k.a. HPMC or hypromellose), hydroxypropyl cellulose, ethylene glycol polymers, and hyaluronic acid (a.k.a. hyaluronan, HA), and tear ointments such as white petrolatum, mineral oil, and similar lubricants can also be included in the compositions. These additional therapeutic agents can be included in known therapeutic amounts, or sub-therapeutic amounts.

Containers and Kits

In some embodiments, the composition is provided in a kit comprising one or more multi-use containers. In some embodiments, the multi-use container comprises a protective cap and a liquid storage bottle, wherein the cap is connected to the bottle via a flexible connector. A blocking plug is arranged in the middle of the top surface of the protective cap. A conical, or other suitable shape, liquid outlet is arranged in the middle of the bottle cover and is tightly matched with the blocking plug of the protective cap. Thus, the sterile composition may be placed into the container for multiple uses.

In some embodiments, the amount of the composition in the container is, or is about: 0.1-0.5, 0.5-1.0, 1-2, 2-5, 5-10, 10-20, 20-30, or 30-60 mL or ranges in between. Containers may be bottles, tubes, vials or other suitable containers. Multi-use containers may be accompanied by instructions to use for a 12 hour, 24 hour, 2-7 day cycle, one month cycle or until a stated expiration date. A single-use container may be suitable for use in one eye or both eyes for a single application cycle.

In some embodiments, the composition is provided in a in a kit comprising a single-use container. In some embodiments, the composition is provided in a kit comprising a plurality of single-use containers. In some embodiments, the single-use container comprises a vessel for holding liquid, a removable seal top for sealing the vessel, and, optionally, a neck portion interconnecting the vessel and the seal top. Kits comprises multiple single-use containers along with instructions to use are provided in several embodiments.

In some embodiments, the container comprises a pharmaceutically inert material. In some embodiments, the container comprises glass, polyvinyl chloride, polypropylene, polyethylene terephthalate, polyethylene terephthalate, polyethylene terephthalate G, high-density polyethylene, low-density polyethylene, polybutylene terephthalate, polyurethane, polyethylene vinyl acetate, silicone, acrylonitrile butadiene styrene, polytetrafluoroethylene, polycarbonate, polystyrene, polymethylmethacrylate, polysulfone, polyvinylidene chloride, or combinations thereof.

In some embodiments, the container comprises polyvinyl chloride, polypropylene, low-density polyethylene, polyurethane, polyethylene vinyl acetate, silicone, or combinations thereof.

In some embodiments, the amount of composition in the container is, or is about, 0.02 mL; 0.05 mL to 1 mL; 0.1 mL to 0.95 mL; 0.15 mL to 0.8 mL; 0.2 mL to 0.85 mL; 0.25 mL to 0.8 mL; 0.3 mL to 0.75 mL; 0.35 mL to 0.7 mL; 0.4 mL to 0.65 mL; 0.45 mL to 0.6 mL; 0.5 mL to 0.55 mL; or any amount in between.

In some embodiments, the amount of composition in the container is, or is about, 0.02 mL; 0.025 mL; 0.030 mL; 0.035 mL; 0.040 mL; 0.045 mL; 0.050 mL; 0.055 mL; 0.060 mL; 0.065 mL; 0.070 mL; 0.075 mL; 0.1 mL; 0.15 mL; 0.2 mL; 0.25 mL; 0.3 mL; 0.35 mL; 0.4 mL; 0.45 mL; 0.5 mL; 0.55 mL; 0.6 mL; 0.65 mL; 0.7 mL; 0.75 mL; 0.8 mL; 0.85 mL; 0.9 mL; 0.95 mL; or 1 mL of the composition, or an amount that is within a range defined by any two of the preceding values.

Ophthalmic and Other Administration

In some embodiments, the composition is administered topically to the eye. In some embodiments, the composition is administered to an individual suffering from any form of dry eye, or dry eye (or other symptoms, such as dry mouth) associated with Sjogren's Syndrome, for the treatment thereof. In some embodiments it is administered as an oral rinse, tab, patch, spray or lozenge to the mouth. The compositions described herein can be provided as liquids (solutions, gels, ointments etc.) or in other suitable forms, such as powders or on patches, tabs, etc. In some embodiments, the compositions described herein are used to achieve one or more of the following: restore basal tearing, salivation, general mucosal and ocular surface wetness; restore ocular surface and mucosal homeostasis, rapidly but transiently promote autophagy to eliminate pressure, stress or degenerative disease throughout the eye and in other organs; reduce inflammation, promote wound healing (such as corneal post refractive surgery or oral wound healing), stabilize the tear lipid layer and suppress bacterial infection.

In some embodiments, administration topically to the eye comprises administering one or more drops of the composition to the surface of the eye. For example, in one embodiment, a user is instructed to apply to the eye surface, and not to a contact lens). In other embodiments, the drops (or other application) is suitable for administration while wearing contact lenses. In some embodiments, the composition is administered from the container as a single dose delivered as a single drop to each eye. In some embodiments, the drop is about 0.020 mL to about 0.050 mL, or any volume in between. In some embodiments, the drop is about 0.035 mL.

In some embodiments, the administration of the composition to the eye improves one or more patient reported symptoms or clinical signs of dry eye or Sjogren's Syndrome. Improvements in dry eye symptoms or signs can be assessed by one or more of the following:

Fluorescein corneal staining (FCS) (0 to 3 scale by region, for 5 regions, total 0-15 scale, using the NEI/Industry Workshop scale)

Lissamine green conjunctival staining (LGCS) (0 to 3 scale by region, total 0-18 scale, using NEI/Industry Workshop scale)

Anesthetized Schirmer test (mm of wetting in 5 minutes), Tear film break-up time (number of seconds)

Eye dryness as reported by the patient on a visual analog scale and tabulated as a mean change from baseline Dry eye-related ocular symptoms questionnaire (SANDE: how frequent and how severe are dry eye symptoms), (Schaumberg D, et al. Development and Validation of a Short Global Dry Eye Symptom Index. The Ocular Surface. January 2007, Vol 5; 1; 50-57, incorporated herein by reference in its entirety).

In some embodiments, the composition is a sterile aqueous composition comprising, consisting or consisting essentially of about 0.001% to about 0.05% of Lacripep™ (SEQ ID NO. 1) or the other peptides identified herein; about 0.001% to about 0.015% anhydrous citric acid; about 0.02% to about 0.40% sodium citrate dihydrate; about 0.0005% to about 0.005% disodium EDTA; about 0.005% to about 0.15% tyloxapol, and about 0.005% to about 0.1% methylparaben; wherein the pH of the composition is adjusted using NaOH or HCl to be about 6.2 pH to about 6.8 pH, and the osmolality of the composition is adjusted using NaCl to be between about 250 to about 350 mOsm/kg. In some embodiments, the amount of NaCl is about 0.1% to about 1%. In an embodiment, the composition does not include methylparaben. In an embodiment, the composition consists of only the listed ingredients, and does not contain any additional active ingredients, excipients (e.g., viscosity building agents, buffering agents, chelating agents, stabilizing agents, preservatives, surfactants, and tonicity agents), carriers or diluents.

In some embodiments, the composition is a sterile aqueous composition comprising, consisting or consisting essentially of about 0.001% to about 0.05% of Lacripep™ (SEQ ID NO. 1) or the other peptides identified herein; about 0.001% to about 0.015% anhydrous citric acid; about 0.02% to about 0.40% sodium citrate dihydrate; about 0.0005% to about 0.005% disodium EDTA; and about 0.005% to about 0.15% tyloxapol; wherein the pH of the composition is adjusted using NaOH or HCl to be about 6.2 pH to about 6.8 pH, and the osmolality of the composition is adjusted using NaCl to be between about 250 to about 350 mOsm/kg. In some embodiments, the amount of NaCl is about 0.1% to about 1%. In an embodiment, the composition consists of only the listed ingredients, and does not contain any additional active ingredients, excipients (e.g., viscosity building agents, buffering agents, chelating agents, stabilizing agents, preservatives, surfactants, and tonicity agents), carriers or diluents.

In some embodiments, the composition is a sterile aqueous composition comprising about 0.01%±0.001% of Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

In some embodiments, the composition is a sterile aqueous composition comprising about 0.005%±0.0005% Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

In some embodiments, the composition is a sterile aqueous composition comprising about 0.001%±0.0001% Lacripep™ (SEQ ID NO. 1) or the other peptides identified herein; about 0.0098%±0.001% anhydrous citric acid; about 0.279%±0.028% sodium citrate dihydrate; about 0.001%±0.0001% disodium EDTA; about 0.05%±0.005% tyloxapol; wherein the pH of the composition is adjusted using NaOH or HCl to be between about 6.2 to about 6.8. and the osmolality of the composition is adjusted using NaCl to be between about 250 to about 350 mOsm/kg. In some embodiments, the amount of NaCl is about 0.50%±0.05%.

Some embodiments include a method of treating Dry Eye and/or Primary Sjogren's Syndrome comprising administering a composition disclosed herein to the eye of a subject having Dry Eye and/or Primary Sjogren's Syndrome. In one embodiment, the compositions described herein are used to treat Sjogren's syndrome. In some embodiments, the compositions described herein are used to treat a subject with one or more of the following criteria:

I. Ocular Symptoms
  Symptoms of dry eyes for at least 3 months
  A foreign body sensation in the eyes
  Use of artificial tears 3 or more times per day
II. Oral Symptoms
  Symptoms of dry mouth for at least 3 months
  Recurrent or persistently swollen salivary glands
  Need for liquids to swallow dry foods
III. Ocular Signs
  Abnormal Anesthetized Schirmer test, (without anesthesia; ≤5 mm/5 minutes)
  Positive vital dye staining of the eye surface
IV. Histopathology
  Lip biopsy showing focal lymphocytic sialoadenitis (focus score≥1 per 4 mm2)
V. Oral Signs
  Unstimulated whole salivary flow (≤1.5 mL in 15 minutes)
  Abnormal parotid sialography
  Abnormal salivary scintigraphy
VI. Autoantibodies
  Anti-SSA (Ro) (Anti-Sjogren's-syndrome-related antigen A) or Anti-SSB
  (La) (Anti-Sjogren's-syndrome-related antigen B), or both.

In one embodiment, the compositions described herein are used to treat subjects that have at least one criteria from each of the six categories above. In some embodiments, the polypeptide or pharmaceutically acceptable salt thereof in the composition is Lacripep™ (having a sequence consisting of Ac-Lys-Gln-Phe-Ile-Glu-Asn-Gly-Ser-Glu-Phe-Ala-Gln-Lys-Leu-Leu-Lys-Lys-Phe-Ser-NH$_2$, where "Ac" represents an acetyl group and the C-terminus is amidated (SEQ ID NO: 1)) in an amount of 0.005%, or 0.01%. In some embodiments, the ophthalmic solution further comprises Citric Acid (about 0.0098% anhydrous), Sodium Citrate (about 0.279% sodium citrate dehydrate), EDTA Disodium (about 0.001%), NaCl (to about 300 mOsm/kg), Tyloxapol (about 0.05%), NaOH (to about 6.5 pH), Purified Water, USP in addition to the polypeptide, e.g., Lacripep™. For assessing efficacy, some embodiments utilize a placebo comprising a vehicle ophthalmic solution without the polypeptide. In some embodiments one drop of the composition is administered to the eye of the subject up to three times daily. In some embodiments, the administration improves the FCS total score (NEI/Industry Workshop 0-15 scale) in the subject's eye after at least two weeks of treatment, or after at least four weeks of treatment, or after at least six weeks from the start of four weeks of treatment, compared to a baseline measure prior to starting treatment. In some embodiments, the administration improves one or more of:

eye dryness after at least two weeks of treatment, or after at least four weeks of treatment, compared to baseline on a visual analog scale;

SANDE (global scores SANDE 1) after at least two weeks of treatment compared to a baseline measure prior to starting treatment;

Mean Scores for SANDE (global scores SANDE-1) after at least two weeks of treatment compared to a baseline measure prior to starting treatment;

Individual Symptom Assessments (Instantaneous) after at least two weeks of treatment compared to a baseline measure prior to starting treatment;

Mean Scores for Individual Symptom Assessments (Reflective) after at least two weeks of treatment compared to a baseline measure prior to starting treatment;

LGCS in the subject's eye after at least two weeks of treatment compared to a baseline measure prior to starting treatment;

Anesthetized Schirmer test in the subject's eye after at least two weeks of treatment compared to a baseline measure prior to starting treatment;

TFBUT in the subject's eye after at least two weeks of treatment compared to a baseline measure prior to starting treatment;

FCS in the subject's eye after at least two weeks of treatment compared to a baseline measure prior to starting treatment;

SANDE (global scores for SANDE 1) after at least 2 weeks of treatment, or after at least 4 weeks of treatment, or 1 week after 4 weeks treatment compared to a baseline measure prior to starting treatment;

Individual Symptoms (Instantaneous) after at least 2 weeks of treatment, or after at least 4 weeks of treatment, or 1 week after 4 weeks treatment compared to a baseline measure prior to starting treatment;

Mean Scores for (global scores SANDE-2) after at least 2 weeks of treatment, or after at least 4 weeks of treatment, or 1 week after 4 weeks treatment compared to a baseline measure prior to starting treatment;

Mean Scores for Individual Symptom Assessments (Reflective) after at least 2 weeks of treatment, or after at least 4 weeks of treatment, or 1 week after 4 weeks treatment compared to a baseline measure prior to starting treatment;

FCS and SANDE 1 and Individual Symptom Assessments (Instantaneous) after at least 2 weeks of treatment, or after at least 4 weeks of treatment, compared to a baseline measure prior to starting treatment;

LGCS after at least 2 weeks of treatment, or after at least 4 weeks of treatment compared to a baseline measure prior to starting treatment;

Anesthetized Schirmer test results after at least 2 weeks of treatment, or after at least 4 weeks of treatment, compared to a baseline measure prior to starting treatment;

TFBUT after at least 2 weeks of treatment, or after at least 4 weeks of treatment, or 1 week after 4 weeks treatment compared to a baseline measure prior to starting treatment.

In some embodiments, the comparison instead, or further, comprises a comparison to a vehicle control.

In one embodiment, any one or more of the following drugs/therapies are not co-administered with the compositions described herein, and in one embodiment any one or more of the following drugs/therapies are co-administered with the with the compositions described herein:

Ophthalmic drugs (any topical eye medications) including prescription medication and over-the-counter [OTC] agents Contact lenses Any ocular surface or eyelid operative procedure within 365 days prior to start of treatment or intraocular surgery within 90 days prior to start of treatment.

amiodarone.

topical ocular antihistamines ocular, inhaled or intranasal corticosteroids topical or oral mast cell stabilizers oral antihistamines topical or nasal vasoconstrictors topical ocular NSAIDs topical ocular antibiotics Within 60 days prior to and/or during treatment: topical cyclosporine, topical lifitegrast Within 90 days prior to and/or during treatment: cauterization of the punctum or alternations to (insertion or removal) punctal plug(s) or nasolacrimal surgery.

Chronic oral anti-viral medications for ocular herpetic disease.

EXAMPLES

The following are non-limiting examples of some of the embodiments described herein.

Example 1—Peptide Composition Stability

Several Lacripep™ (SEQ ID NO. 1) ophthalmic formulations were tested for stability at one week, two weeks, one, two, three, four months, and 12 months at −20° C., 5° C., 25° C./25% relative humidity or 25° C./60% relative humidity. These formulations are shown in Table 1.5, and the stability data are shown in Table 2 (with degradation products indicated as a w/w percentage of the initial amount of Lacripep™) and Table 3 (12 month data). In all conditions tested, each formulation remained a clear, colorless solution, and the packaging did not leak or become discolored.

TABLE 1.5

Lacripep ™ Formulations for Stability Studies

| Component (% w/w) | F1 | F2 | G1 | G2 | Vehicle |
|---|---|---|---|---|---|
| Lacripep ™ (SEQ ID NO. 1) | 0.01 | 0.001 | 0.01 | 0.001 | — |
| Methylparaben | 0.04 | 0.04 | 0.04 | 0.04 | 0.04 |
| Citric Acid (Anhydrous) | 0.0098 | 0.0098 | 0.0098 | 0.0098 | 0.0098 |
| Sodium Citrate (Anhydrous) | 0.279 | 0.279 | 0.279 | 0.279 | 0.279 |
| EDTA Disodium | 0.001 | 0.001 | 0.001 | 0.001 | 0.001 |
| Polysorbate 80 (super refined) | 0.1 | 0.1 | — | — | 0.1 |
| Tyloxapol | — | — | 0.05 | 0.05 | 0.05 |
| Povidone K30 | — | — | — | — | 0.5 |

TABLE 1.5-continued

Lacripep ™ Formulations for Stability Studies

| Component (% w/w) | F1 | F2 | G1 | G2 | Vehicle |
|---|---|---|---|---|---|
| 10% NaOH (aq) | q.s. pH 6.5 ± 0.3 | | | | |
| 20% NaCl Solution | q.s. 300 ± 20 mOsm/L | | | | |
| Purified Water | qsad 100 | qsad 100 | qsad 100 | qsad 100 | qsad 100 |

TABLE 2

Lacripep ™ Formulation Stability, pH and Degradation Product % w/w

| Timepoint | Storage | F1 | F2 | G1 | G2 |
|---|---|---|---|---|---|
| 0 | — | pH = 6.2 0% | pH = 6.3 0% | pH = 6.3 0% | pH = 6.3 0% |
| 1 wk | 5° C. | — 0.0105% | — 0.0010% | — 0.0106% | — 0.0010% |
|  | 25° C./25% RH | — 0.099% | — 0.0009% | — 0.010% | — 0.0010% |
| 2 wk | 25° C./25% RH | — 0.0091% | — 0.0008% | — 0.0093% | — 0.009% |
| 1 mo | 5° C. | pH = 6.4 0.0112% | pH = 6.3 0.0010% | pH = 6.5 0.0112% | pH = 6.3 0.0011% |
|  | 25° C./25% RH | pH = 6.3 0.0091% | pH = 6.4 0.0008% | pH = 6.3 0.0092% | pH = 6.3 0.0009% |
| 2 mo | 5° C. | — 0.010% | — 0.00089% | — 0.010% | — 0.00093% |
| 3 mo | −20° C. | — 0.0106% | — 0.0009% | — 0.0109% | — 0.001% |
|  | 5° C. | pH = 6.2 0.01% | pH = 6.3 0.0009% | pH = 6.2 0.0101% | pH = 6.3 0.0009% |
| 4 mo | 5° C. | — 0.0097% | — 0.0009% | — 0.0097% | — 0.0009% |
| 5 mo | 5° C. | — 0.0094% | — 0.0007% | — 0.0097% | — 0.0006% |

TABLE 3

Lacripep ™ Formulation Stability at 12 months, 5° C.

| Formulation (Initial Lacripep % w/w) | Storage | Avg. Lacripep % w/w | Degradation Products RRT | Avg. % w/w | pH |
|---|---|---|---|---|---|
| F1 (0.01 w/w) | 5° C. | 0.0088 | 0.95 0.97 | 0.0001 0.0007 | 6.2 |
| F2 (0.001% w/w) | 5° C. | 0.0007 | N/A | N/A | 6.2 |
| G1 (0.01% w/w) | 5° C. | 0.0091 | 0.95 0.97 | 0.0002 0.0008 | 6.2 |
| G2 (0.001% w/w) | 5° C. | 0.0008 | N/A | N/A | 6.3 |

RRT = relative retention time

Example 2—Comparative Peptide Stability

Lacripep™ (SEQ ID NO. 1) stability was assessed in PBS at pH 4.5 and 7.0 (FIG. 1) and citrate buffer at pH 6.0 and 6.5 (FIG. 2). The initial concentration of Lacripep™ was 0.001%, and each trial was run at 60° C. The stability was assessed using MALDI TOF mass spectrometry at the initiation of the experiment (week 0, FIGS. 1A and 2A) and after two weeks (week 2, FIGS. 1B and 2B). After 2 weeks in PBS at pH 4.5 and 7.0, significant degradation was observed in the Lacripep™ peak (large arrow) as indicated by the appearance of new lower m/e peaks, for example at 993.9 (m/e) (small arrows, FIG. 1B). In contrast after 2 weeks in citrate buffer at pH 6.0 and 6.5, there was no change in the intensity of the Lacripep™ peak (large arrow), or the appearance of any new lower m/e peaks (FIG. 2B). This demonstrates the unexpected improvement in peptide stability in citrate buffer.

Example 3—Composition Manufacturing Process

Table 4 summarizes the process described below.

In an appropriate size of manufacturing vessel, add sterile purified water (Part I) and methylparaben. With propeller mixing, heat the mixture to 65° C.±5° C. until the methylyparaben is dissolved and a clear solution is achieved, then remove from heat. If necessary to obtain a clear solution, the mixture may be heated up to 80° C.±2° C.

With further continuous propeller mixing, add citric acid, sodium citrate, and EDTA disodium. Mix until all three ingredients are dissolved, a clear solution is obtained and the temperature of the solution is less than 22° C.±2° C.

With further continuous propeller mixing, add Tyloxapol and Lacripep™ (SEQ ID NO. 1) and mix until a clear solution is obtained.

Adjust the pH of the bulk solution to 6.5±0.3 with either 10% NaOH (aq) or 10% HCl (aq), as necessary. Mix until the solution is homogeneous.

Adjust the osmolality of the solution to 300±20 mOsm/kg with 25% NaCl (aq), as necessary.

Add purified water (Part II) to the batch to q.s. the batch to 100%. Mix with a propeller until the solution is homogeneous.

TABLE 4

Process (A)

| Component (% w/w) | Active Composition | Control Composition (vehicle only) |
|---|---|---|
| Lacripep ™ (SEQ ID NO. 1) | 0.01 | 0 |
| Citric Acid (Anhydrous) | 0.0098 | 0.0098 |
| Sodium Citrate (Dihydrate) | 0.279 | 0.279 |
| EDTA Disodium | 0.001 | 0.001 |
| Tyloxapol | 0.05 | 0.05 |
| Methylparaben | 0.04 | |
| 10% NaOH (aq) or 10% HCl (aq) | Adjust pH to 6.5 ± 0.3 | |
| 25% NaCl Solution | Qs ad Osmolality to 300 ± 20 mOsm/kg | |
| Sterile Purified Water | qs ad 100 | qs ad 100 |

Example 4—Composition Manufacturing Process—Preservative Free Composition

Table 5 summarizes the process described below.

In an appropriate size of manufacturing vessel, add purified water (Part I). With continuous propeller mixing, add citric acid, sodium citrate, and EDTA disodium. Mix until all three ingredients are dissolved, a clear solution is obtained and the temperature of the solution is less than 22° C.±2° C.

With further continuous propeller mixing, add Tyloxapol and Lacripep™ (SEQ ID NO. 1) and mix until a clear solution is obtained.

Adjust the pH of the bulk solution to 6.5±0.3 with either 10% NaOH (aq) or 10% HCl (aq), as necessary. Mix until the solution is homogeneous.

Adjust the osmolality of the solution to 300±20 mOsm/kg with 25% NaCl (aq), as necessary.

TABLE 5

Process (B)

| Component (% w/w) | Active Composition | Control Composition (vehicle only) |
|---|---|---|
| Lacripep ™ (SEQ ID NO. 1) | 0.01 | 0 |
| Citric Acid (Anhydrous) | 0.0098 | 0.0098 |
| Sodium Citrate (Dihydrate) | 0.279 | 0.279 |
| EDTA Disodium | 0.001 | 0.001 |
| Tyloxapol | 0.05 | 0.05 |
| 10% NaOH (aq) or 10% HCl (aq) | Adjust pH to 6.5 ± 0.3 | |
| 25% NaCl Solution | Qs ad Osmolality to 300 ± 20 mOsm/kg | |
| Sterile Purified Water | Qs ad 100 | Qs ad 100 |

Example 5—Composition Manufacturing Process

Table 6 summarizes the process described below.

In an appropriate size of manufacturing vessel, add purified water (Part I). With continuous propeller mixing, add citric acid, sodium citrate, and EDTA disodium. Mix until all three ingredients are dissolved, a clear solution is obtained and the temperature of the solution is less than 22° C.±2° C.

With further continuous propeller mixing, add Tyloxapol and Lacripep™ (SEQ ID NO. 1) and mix until a clear solution is obtained.

Adjust the pH of the bulk solution to 6.5±0.3 with either 10% NaOH (aq) or 10% HCl (aq), as necessary. Mix until the solution is homogeneous.

Adjust the osmolality of the solution to 300±20 mOsm/kg with 25% NaCl (aq), as necessary.

TABLE 6

Process (C)

| Component (% w/w) | Active Composition | Control Composition (vehicle only) |
|---|---|---|
| Lacripep ™ (SEQ ID NO. 1) | 0.001% to 0.05% | 0 |
| Citric Acid (Anhydrous) | 0.001% to 0.015% | 0.001% to 0.015% |
| Sodium Citrate (Dihydrate) | 0.02 to 0.40% | 0.02 to 0.40% |
| EDTA Disodium | 0.0005% to 0.005% | 0.0005% to 0.005% |
| Tyloxapol | 0.005% to 0.15% | 0.005% to 0.15% |
| 10% NaOH (aq) or 10% HCl (aq) | Adjust pH to 6.5 ± 0.3 | |

TABLE 6-continued

Process (C)

| | Composition | |
|---|---|---|
| Component (% w/w) | Active Composition | Control Composition (vehicle only) |
| 25% NaCl Solution | Qs ad Osmolality to 300 ± 20 mOsm/kg | |
| Sterile Purified Water | Qs ad 100 | Qs ad 100 |

For example, the composition comprises less than 0.05% of an active ingredient such as a polypeptide (e.g., 0.001-0.02%, 0.001-0.05%), or a pharmaceutically acceptable salt thereof; and one or more of the following: (i) less than 0.6% of a buffer (e.g., 0.001-0.3%, 0.001-0.6%); (ii) less than 0.01% disodium EDTA (e.g., 0%, 0.001-0.005%, 0.001-0.01%); and (iii) less than 0.1% tyloxapol (e.g., 0%, 0.001-0.05%, 0.001-0.1%), as well optional other ingredients.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the embodiments of the invention(s).

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like.

The indefinite article "a" or "an" does not exclude a plurality. The use of "about" before a number includes the number itself. For example, "about 5" provides express support for "5".

```
SEQUENCE LISTING

<160> NUMBER OF SEQ ID NOS: 9

<210> SEQ ID NO 1
<211> LENGTH: 19
<212> TYPE: PRT
<213> ORGANISM: Homo sapiens
<220> FEATURE:
<221> NAME/KEY: ACETYLATION
<222> LOCATION: 1
<220> FEATURE:
<221> NAME/KEY: AMIDATION
<222> LOCATION: 19

<400> SEQUENCE: 1

Lys Gln Phe Ile Glu Asn Gly Ser Glu Phe Ala Gln Lys Leu Leu Lys
1               5                   10                  15

Lys Phe Ser

<210> SEQ ID NO 2
<211> LENGTH: 25
<212> TYPE: PRT
<213> ORGANISM: Homo sapiens
<220> FEATURE:
<221> NAME/KEY: ACETYLATION
<222> LOCATION: 1
<220> FEATURE:
<221> NAME/KEY: AMIDATION
<222> LOCATION: 25

<400> SEQUENCE: 2

Lys Gln Phe Ile Glu Asn Gly Ser Glu Phe Ala Gln Lys Leu Leu Lys
1               5                   10                  15

Lys Phe Ser Leu Leu Lys Pro Trp Ala
            20                  25

<210> SEQ ID NO 3
<211> LENGTH: 138
<212> TYPE: PRT
<213> ORGANISM: Homo sapiens

<400> SEQUENCE: 3

Met Lys Phe Thr Thr Leu Leu Phe Leu Ala Ala Val Ala Gly Ala Leu
1               5                   10                  15
```

```
Val Tyr Ala Glu Asp Ala Ser Ser Asp Ser Thr Gly Ala Asp Pro Ala
                20                  25                  30

Gln Glu Ala Gly Thr Ser Lys Pro Asn Glu Glu Ile Ser Gly Pro Ala
         35                  40                  45

Glu Pro Ala Ser Pro Glu Thr Thr Thr Thr Ala Gln Glu Thr Ser
 50                  55                  60

Ala Ala Ala Val Gln Gly Thr Ala Lys Val Thr Ser Ser Arg Gln Glu
 65                  70                  75                  80

Leu Asn Pro Leu Lys Ser Ile Val Glu Lys Ser Ile Leu Leu Thr Glu
                 85                  90                  95

Gln Ala Leu Ala Lys Ala Gly Lys Gly Met His Gly Gly Val Pro Gly
            100                 105                 110

Gly Lys Gln Phe Ile Glu Asn Gly Ser Glu Phe Ala Gln Lys Leu Leu
            115                 120                 125

Lys Lys Phe Ser Leu Leu Lys Pro Trp Ala
            130                 135
```

<210> SEQ ID NO 4
<211> LENGTH: 119
<212> TYPE: PRT
<213> ORGANISM: Homo sapiens

<400> SEQUENCE: 4

```
Glu Asp Ala Ser Ser Asp Ser Thr Gly Ala Asp Pro Ala Gln Glu Ala
 1               5                  10                  15

Gly Thr Ser Lys Pro Asn Glu Glu Ile Ser Gly Pro Ala Glu Pro Ala
            20                  25                  30

Ser Pro Pro Glu Thr Thr Thr Thr Ala Gln Glu Thr Ser Ala Ala Ala
         35                  40                  45

Val Gln Gly Thr Ala Lys Val Thr Ser Ser Arg Gln Glu Leu Asn Pro
 50                  55                  60

Leu Lys Ser Ile Val Glu Lys Ser Ile Leu Leu Thr Glu Gln Ala Leu
 65                  70                  75                  80

Ala Lys Ala Gly Lys Gly Met His Gly Gly Val Pro Gly Gly Lys Gln
                 85                  90                  95

Phe Ile Glu Asn Gly Ser Glu Phe Ala Gln Lys Leu Leu Lys Lys Phe
            100                 105                 110

Ser Leu Leu Lys Pro Trp Ala
            115
```

<210> SEQ ID NO 5
<211> LENGTH: 114
<212> TYPE: PRT
<213> ORGANISM: Homo sapiens

<400> SEQUENCE: 5

```
Asp Ser Thr Gly Ala Asp Pro Ala Gln Glu Ala Gly Thr Ser Lys Pro
 1               5                  10                  15

Asn Glu Glu Ile Ser Gly Pro Ala Glu Pro Ala Ser Pro Pro Glu Thr
            20                  25                  30

Thr Thr Thr Ala Gln Glu Thr Ser Ala Ala Ala Val Gln Gly Thr Ala
         35                  40                  45

Lys Val Thr Ser Ser Arg Gln Glu Leu Asn Pro Leu Lys Ser Ile Val
 50                  55                  60

Glu Lys Ser Ile Leu Leu Thr Glu Gln Ala Leu Ala Lys Ala Gly Lys
 65                  70                  75                  80
```

-continued

```
Gly Met His Gly Gly Val Pro Gly Gly Lys Gln Phe Ile Glu Asn Gly
             85                  90                  95

Ser Glu Phe Ala Gln Lys Leu Leu Lys Lys Phe Ser Leu Leu Lys Pro
            100                 105                 110

Trp Ala

<210> SEQ ID NO 6
<211> LENGTH: 114
<212> TYPE: PRT
<213> ORGANISM: Homo sapiens

<400> SEQUENCE: 6

Glu Asp Ala Ser Ser Asp Ser Thr Gly Ala Asp Pro Ala Gln Glu Ala
1               5                  10                  15

Gly Thr Ser Lys Pro Asn Glu Glu Ile Ser Gly Pro Ala Glu Pro Ala
            20                  25                  30

Ser Pro Pro Glu Thr Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu Lys Lys Phe
            100                 105                 110

Ser Leu

<210> SEQ ID NO 7
<211> LENGTH: 109
<212> TYPE: PRT
<213> ORGANISM: Homo sapiens

<400> SEQUENCE: 7

Glu Asp Ala Ser Ser Asp Ser Thr Gly Ala Asp Pro Ala Gln Glu Ala
1               5                  10                  15

Gly Thr Ser Lys Pro Asn Glu Glu Ile Ser Gly Pro Ala Glu Pro Ala
            20                  25                  30

Ser Pro Pro Glu Thr Thr Thr Thr Ala Gln Glu Thr Ser Ala Ala Ala
        35                  40                  45

Val Gln Gly Thr Ala Lys Val Thr Ser Ser Arg Gln Glu Leu Asn Pro
    50                  55                  60

Leu Lys Ser Ile Val Glu Lys Ser Ile Leu Leu Thr Glu Gln Ala Leu
65                  70                  75                  80

Ala Lys Ala Gly Lys Gly Met His Gly Gly Val Pro Gly Gly Lys Gln
                85                  90                  95

Phe Ile Glu Asn Gly Ser Glu Phe Ala Gln Lys Leu Leu
            100                 105

<210> SEQ ID NO 8
<211> LENGTH: 104
<212> TYPE: PRT
<213> ORGANISM: Homo sapiens

<400> SEQUENCE: 8

Glu Asp Ala Ser Ser Asp Ser Thr Gly Ala Asp Pro Ala Gln Glu Ala
1               5                  10                  15
```

-continued

```
Gly Thr Ser Lys Pro Asn Glu Glu Ile Ser Gly Pro Ala Glu Pro Ala
            20              25              30

Ser Pro Pro Glu Thr Thr Thr Thr Ala Gln Glu Thr Ser Ala Ala Ala
            35              40              45

Val Gln Gly Thr Ala Lys Val Thr Ser Ser Arg Gln Glu Leu Asn Pro
        50              55              60

Leu Lys Ser Ile Val Glu Lys Ser Ile Leu Leu Thr Glu Gln Ala Leu
65              70              75              80

Ala Lys Ala Gly Lys Gly Met His Gly Gly Val Pro Gly Gly Lys Gln
            85              90              95

Phe Ile Glu Asn Gly Ser Glu Phe
            100

<210> SEQ ID NO 9
<211> LENGTH: 14
<212> TYPE: PRT
<213> ORGANISM: Homo sapiens

<400> SEQUENCE: 9

Asn Gly Ser Glu Phe Ala Gln Lys Leu Leu Lys Lys Phe Ser
1               5               10
```

What is claimed is:

1. An aqueous liquid composition comprising:
    0.0001-0.006% weight/weight (w/w) of a polypeptide, or an equivalent amount of a pharmaceutically acceptable salt thereof;
    0.2-0.4% (w/w) of a citrate buffer;
    0.0005-0.005% (w/w) of disodium EDTA;
    no, or 0.01-0.1% (w/w) of tyloxapol,
    and a tonicity agent;
    wherein the polypeptide or pharmaceutically acceptable salt thereof comprises a polypeptide having an amino acid sequence consisting of SEQ ID NO: 1,
    wherein the pH of the composition is 6.4 to 6.6 and the osmolality of the composition is 150 to 350 mOsm/kg, and
    wherein the aqueous liquid composition is sterile.

2. The aqueous composition of claim 1,
    wherein the polypeptide or an equivalent amount of a pharmaceutically acceptable salt thereof is 0.0001% to 0.0005% (w/w), 0.00075% to 0.002% (w/w) or 0.004% to 0.006% (w/w);
    wherein the disodium EDTA is 0.0008% to 0.002% (w/w); and
    wherein the tyloxapol is 0.04% to 0.06% (w/w).

3. The aqueous composition of claim 2, wherein the citrate buffer comprises 0.001% to 0.015% (w/w) anhydrous citric acid and 0.02% to 0.40% (w/w) sodium citrate dihydrate.

4. The aqueous composition of claim 3, wherein the pH of the composition is 6.5±0.065%.

5. The aqueous composition of claim 3, wherein the osmolality of the composition is 180 to 210 mOsm/kg.

6. The aqueous composition of claim 5, wherein the tonicity agent is sodium chloride and the amount of NaCl is 0.4% (w/w) to 0.6% (w/w).

7. The aqueous composition of claim 6, wherein the amount of NaCl is 0.5% (w/w).

8. The aqueous composition of claim 1, wherein the composition further comprises 0.04% (w/w) methylparaben.

9. The aqueous composition of claim 1, wherein the N-terminus of the polypeptide is acetylated and the C-terminus of the polypeptide is amidated.

10. The aqueous composition of claim 9,
    wherein the polypeptide is 0.00025%±0.000025% w/w, 0.001%±0.0001% w/w, or 0.005%±0.0005% (w/w), or a pharmaceutically acceptable salt thereof;
    wherein the citrate buffer is 0.2-0.4% (w/w);
    wherein the disodium EDTA is 0.0008-0.002% (w/w); and
    wherein the tyloxapol is 0.04-0.06% (w/w).

11. The aqueous composition claim 1 wherein the composition contains no tyloxapol.

12. The aqueous composition of claim 1, wherein the aqueous composition maintains at least 95% of the polypeptide in undegraded form in said aqueous composition after storage of said aqueous composition for 1 week at 5±3° C. or at least 90% of the polypeptide in undegraded form in said aqueous composition after storage of said aqueous composition for 1 week at 25±2° C. and 25±5% relative humidity.

13. The aqueous liquid composition of claim 1, wherein the composition comprises: 0.00025%±0.000025% w/w, 0.001%±0.0001% w/w, or 0.005%±0.0005% w/w of the polypeptide, or an equivalent amount of a pharmaceutically acceptable salt thereof;
    0.279%±0.028% w/w sodium citrate dihydrate;
    0.0098%±0.001% w/w anhydrous citric acid;
    0.001%±0.0001% w/w disodium EDTA;
    0.05%±0.005% w/w of tyloxapol,
    0.50%±0.05% w/w NaCl;
    wherein the polypeptide or pharmaceutically acceptable salt thereof comprises a polypeptide having an amino acid sequence consisting of SEQ ID NO: 1 wherein the N-terminus of the polypeptide is acetylated, and the C-terminus of the polypeptide is amidated, and
    wherein the pH of the composition is 6.4 to 6.6, and
    wherein the osmolality of the composition is 190±19 mOsm/kg.

14. The aqueous liquid composition of claim 13, wherein the composition comprises 0.005%±0.0005% w/w of the polypeptide, or an equivalent amount of a pharmaceutically acceptable salt thereof.

15. The aqueous liquid composition of claim 13, wherein the composition comprises 0.001%±0.0001% w/w of the polypeptide, or an equivalent amount of a pharmaceutically acceptable salt thereof.

16. The aqueous liquid composition of claim 13, wherein the composition comprises 0.00025%±0.000025% w/w of the polypeptide, or an equivalent amount of a pharmaceutically acceptable salt thereof.

17. The aqueous liquid composition of claim 13, wherein the polypeptide is an acetate salt.

18. The aqueous liquid composition of claim 14, wherein the polypeptide is an acetate salt.

19. The aqueous liquid composition of claim 15, wherein the polypeptide is an acetate salt.

20. The aqueous liquid composition of claim 16, wherein the polypeptide is an acetate salt.

21. The aqueous composition of claim 1, wherein the aqueous composition maintains at least 98% of the polypeptide in undegraded form in said aqueous composition after storage of said aqueous composition for 1 week at 5±3° C. or at least 94% of the polypeptide in undegraded form in said aqueous composition after storage of said aqueous composition for 1 week at 25±2° C. and 25±5% relative humidity.

22. The aqueous composition of claim 1, wherein the composition is in a container configured for a single use having a removable seal top for sealing the container that cannot reseal the container once removed, and wherein the volume of the aqueous composition in the container is 0.05 mL to 1 mL.

23. The aqueous composition of claim 2, wherein the composition does not contain a viscosity building agent.

* * * * *